US008364264B2

(12) United States Patent
Meyer et al.

(10) Patent No.: US 8,364,264 B2
(45) Date of Patent: Jan. 29, 2013

(54) PACING INTERVAL ADJUSTMENT FOR CARDIAC PACING RESPONSE DETERMINATION

(75) Inventors: Scott A. Meyer, Rochester, MN (US); Yanting Dong, Shoreview, MN (US); Kevin J. Stalsberg, White Bear Lake, MN (US); Alok Sathaye, Minneapolis, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 1590 days.

(21) Appl. No.: 11/242,240

(22) Filed: Oct. 3, 2005

(65) Prior Publication Data

US 2007/0078489 A1    Apr. 5, 2007

(51) Int. Cl.
*A61N 1/362* (2006.01)
(52) U.S. Cl. .......................................................... 607/28
(58) Field of Classification Search ................ 607/28, 607/7, 9, 15, 4, 5, 14, 116, 119, 122, 123; 600/372–374, 377, 393, 509, 515, 516, 518, 600/519, 521
See application file for complete search history.

(56) References Cited

U.S. PATENT DOCUMENTS

| | | | | |
|---|---|---|---|---|
| 4,955,376 A * | 9/1990 | Callaghan et al. | ............... | 607/28 |
| 5,340,361 A * | 8/1994 | Sholder | .............................. | 607/24 |
| 5,766,229 A * | 6/1998 | Bornzin | ........................... | 607/28 |
| 5,902,324 A * | 5/1999 | Thompson et al. | ................ | 607/9 |
| 6,221,011 B1 | 4/2001 | Bardy | | |
| 6,270,457 B1 | 8/2001 | Bardy | | |
| 6,277,072 B1 | 8/2001 | Bardy | | |
| 6,280,380 B1 | 8/2001 | Bardy | | |
| 6,312,378 B1 | 11/2001 | Bardy | | |
| 6,336,903 B1 | 1/2002 | Bardy | | |
| 6,358,203 B2 | 3/2002 | Bardy | | |
| 6,368,284 B1 | 4/2002 | Bardy | | |
| 6,398,728 B1 | 6/2002 | Bardy | | |
| 6,440,066 B1 | 8/2002 | Bardy | | |
| 6,456,881 B1 * | 9/2002 | Bornzin et al. | .................. | 607/27 |
| 6,512,953 B2 * | 1/2003 | Florio et al. | ..................... | 607/28 |
| 6,567,701 B2 * | 5/2003 | Vonk | ............................... | 607/28 |
| 7,383,079 B2 * | 6/2008 | Holland | ......................... | 600/509 |
| 2001/0049542 A1 * | 12/2001 | Florio et al. | ..................... | 607/28 |
| 2003/0083711 A1 * | 5/2003 | Yonce et al. | ..................... | 607/27 |
| 2004/0106962 A1 * | 6/2004 | Mai et al. | ......................... | 607/19 |

* cited by examiner

*Primary Examiner* — Carl H Layno
*Assistant Examiner* — Frances Oropeza
(74) *Attorney, Agent, or Firm* — Seager, Tufte & Wickhem, LLC

(57) ABSTRACT

The waveform morphology of a propagated pacing response signal may be adjusted to achieve a waveform morphology that enhances cardiac pacing response determination. One or more pacing intervals may be adjusted to achieve at least one cardiac pacing response waveform morphology that enhances determination of the cardiac pacing response. The heart is paced using the one or more adjusted pacing intervals and the cardiac response to the pacing is determined. The one or more adjusted pacing intervals may include an atrioventricular pacing delay, an interatrial pacing delay, an interventricular pacing delay, or other inter-chamber or inter-site pacing delays. Adjusting the one or more pacing intervals may be used to increase a difference between a first waveform morphology associated with multi-chamber capture and a second waveform morphology associated with single chamber capture.

28 Claims, 14 Drawing Sheets

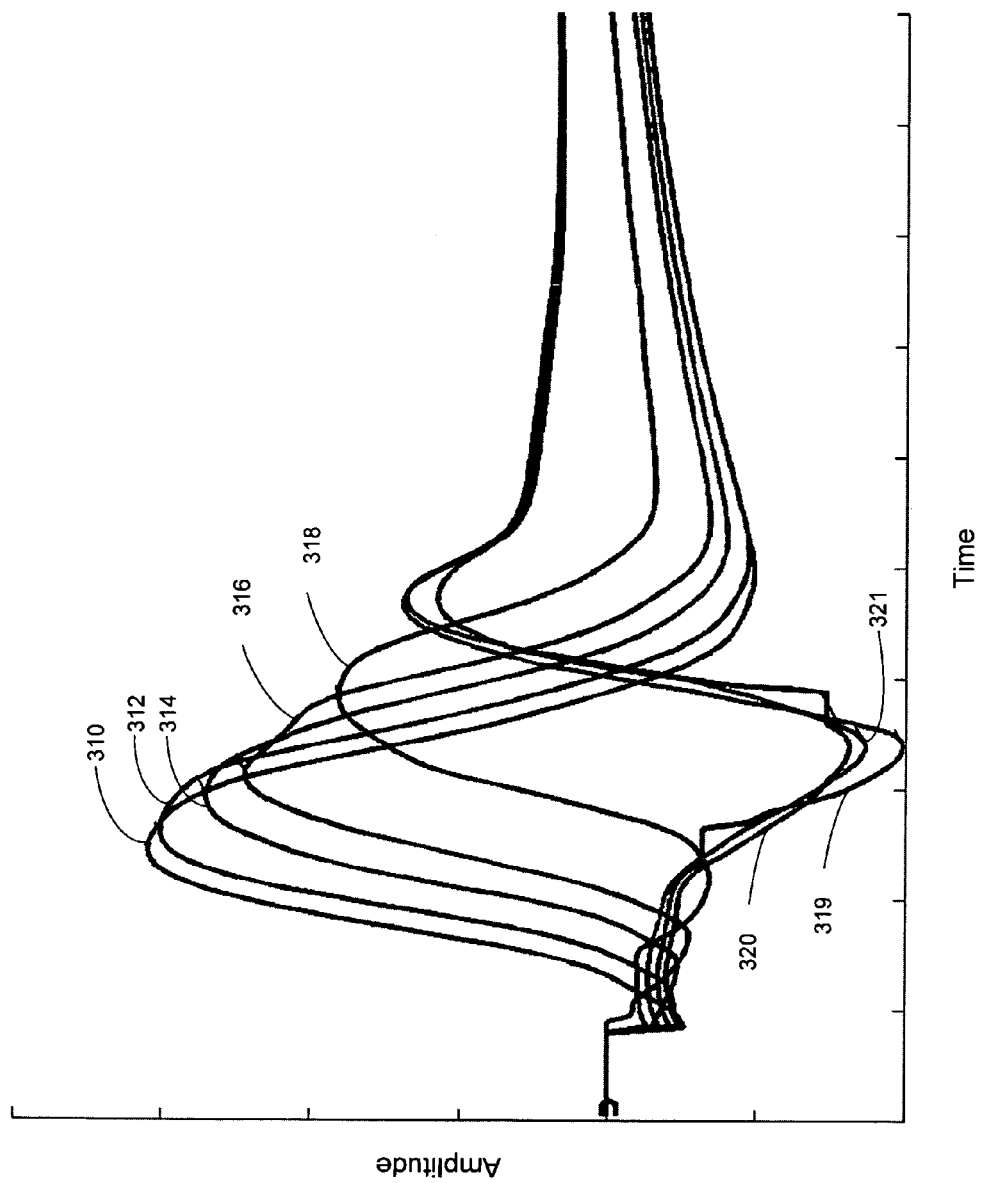

PACING INTERVAL ADJUSTMENT FOR CARDIAC PACING RESPONSE DETERMINATION

FIELD OF THE INVENTION

The present invention relates generally to implantable medical devices and, more particularly, to determination of the cardiac response to pacing.

BACKGROUND OF THE INVENTION

When functioning normally, the heart produces rhythmic contractions and is capable of pumping blood throughout the body. However, due to disease or injury, the heart rhythm may become irregular resulting in diminished pumping efficiency. Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias. These systems typically include circuitry to sense electrical signals from the heart and a pulse generator for delivering electrical stimulation pulses to the heart. Leads extending into the patient's heart are connected to electrodes that contact the myocardium for sensing the heart's electrical signals and for delivering stimulation pulses to the heart in accordance with various therapies for treating the arrhythmias.

Cardiac rhythm management systems operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

When a pace pulse produces a contraction in the heart tissue, the electrical cardiac signal preceding the contraction is denoted the captured response (CR). The captured response typically includes an electrical signal, denoted the evoked response signal, associated with the heart contraction, along with a superimposed signal associated with residual post pace polarization at the electrode-tissue interface. The magnitude of the residual post pace polarization signal, or pacing artifact, may be affected by a variety of factors including lead polarization, after-potential from the pace pulse, lead impedance, patient impedance, pace pulse width, and pace pulse amplitude, for example.

A pace pulse must exceed a minimum energy value, or capture threshold, to produce a contraction. It is desirable for a pace pulse to have sufficient energy to stimulate capture of the heart without expending energy significantly in excess of the capture threshold. Thus, accurate determination of the capture threshold is required for efficient pace energy management. If the pace pulse energy is too low, the pace pulses may not reliably produce a contractile response in the heart and may result in ineffective pacing. If the pace pulse energy is too high, the patient may experience discomfort and the battery life of the device will be shorter.

Detecting if a pacing pulse "captures" the heart and produces a contraction allows the cardiac rhythm management system to adjust the energy level of pace pulses to correspond to the optimum energy expenditure that reliably produces capture. Further, capture detection allows the cardiac rhythm management system to initiate a back-up pulse at a higher energy level whenever a pace pulse does not produce a contraction.

A fusion beat is a cardiac contraction that occurs when two cardiac depolarizations of a particular chamber, but from separate initiation sites, merge. At times, a depolarization initiated by a pacing pulse may merge with an intrinsic beat, producing a fusion beat. Fusion beats, as seen on electrocardiographic recordings, exhibit various morphologies. The merging depolarizations of a fusion beat do not contribute evenly to the total depolarization.

Pseudofusion occurs when a pacing stimulus is delivered on a spontaneous P wave during atrial pacing or on a spontaneous QRS complex during ventricular pacing. In pseudofusion, the pacing stimulus may be ineffective because the tissue around the electrode has already spontaneously depolarized and is in its refractory period.

Discriminating between possible cardiac responses to a pacing stimulus proves difficult when morphologies of the response signals are similar. Erroneous classification of the cardiac response may lead to improper detection of arrhythmias and/or inefficient or improper pacing parameters. The present invention provides methods and systems for improved discrimination of various cardiac pacing responses.

SUMMARY OF THE INVENTION

The present invention is directed to cardiac devices and methods that adjust a pacing interval to alter a propagated signal response to achieve a waveform morphology that enhances cardiac pacing response determination.

One embodiment of the invention involves a method for cardiac pacing response determination. The method includes adjusting one or more pacing intervals to achieve at least one cardiac pacing response waveform that enhances determination of the cardiac pacing response. The heart is paced using the one or more adjusted pacing intervals. The cardiac response to the pacing is determined.

For example, the one or more adjusted pacing intervals may include an atrioventricular pacing delay, an interatrial pacing delay, an interventricular pacing delay, or other interchamber or inter-site pacing delays. In one implementation, the one or more pacing intervals may be adjusted to enhance a difference between a first waveform morphology associated with multi-chamber capture and a second waveform morphology associated with single chamber capture. In another implementation, the one or more pacing intervals may be adjusted to enhance a difference between a first waveform morphology associated with capture of a heart chamber and a second waveform morphology associated with intrinsic depolarization of the heart chamber.

According to one aspect of the invention, a value for a pacing interval that enhances the waveform morphology for cardiac pacing response determination may be determined during an initialization process. The pacing interval is adjusted to the determined value and the capture threshold test is performed using the adjusted pacing interval.

According to another aspect of the invention, the one or more pacing intervals may be adjusted to adapt for temporal drift of the cardiac pacing response waveform morphology.

According to a further aspect of the invention, the one or more pacing intervals may be adjusted to achieve a cardiac pacing response waveform morphology that enhances cardiac pacing response determination in the presence of fusion or noise.

Another embodiment of the invention is directed to a cardiac rhythm management device. The device includes pacing interval circuitry configured to time one or more pacing intervals. The pacing interval circuitry is configured to adjust the one or more pacing intervals to achieve a cardiac response waveform morphology that enhances cardiac pacing response determination. A pulse generator is coupled to the pacing interval circuitry and is configured for pacing the heart using the one or more adjusted pacing intervals. The device includes sensing circuitry configured to sense a cardiac signal. A processor is coupled to the sensing circuitry and is configured to determine the cardiac response to the pacing based on the sensed cardiac signal.

According to one implementation, the pacing interval circuitry is configured to adjust the one or more pacing intervals to enhance a difference in a first waveform morphology associated with a first cardiac pacing response and a second waveform morphology associated with a second cardiac pacing response. In a more specific example of the above implementation, the pacing interval timing circuitry adjusts an interventricular delay, the first cardiac pacing response is biventricular capture, and the second cardiac pacing response comprises right ventricular capture with loss of left ventricular capture.

According to another aspect of the invention, the sensing circuitry comprises one or more electrodes disposed within a heart chamber. The cardiac signal is sensed using the one or more electrodes. The processor discriminates between a multi-chamber cardiac pacing response and a single chamber cardiac pacing response based on the sensed signal. More specifically, the cardiac signal may be sensed using a right ventricular defibrillation electrode. The processor discriminates between biventricular capture and right ventricular only capture based on the cardiac signal sensed at the right ventricular defibrillation electrode.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 3A shows cardiac signals corresponding to biventricular cardiac capture for biventricular pacing with various interventricular delays as sensed from the right ventricular shock channel in accordance with embodiments of the invention;

Figure 1:
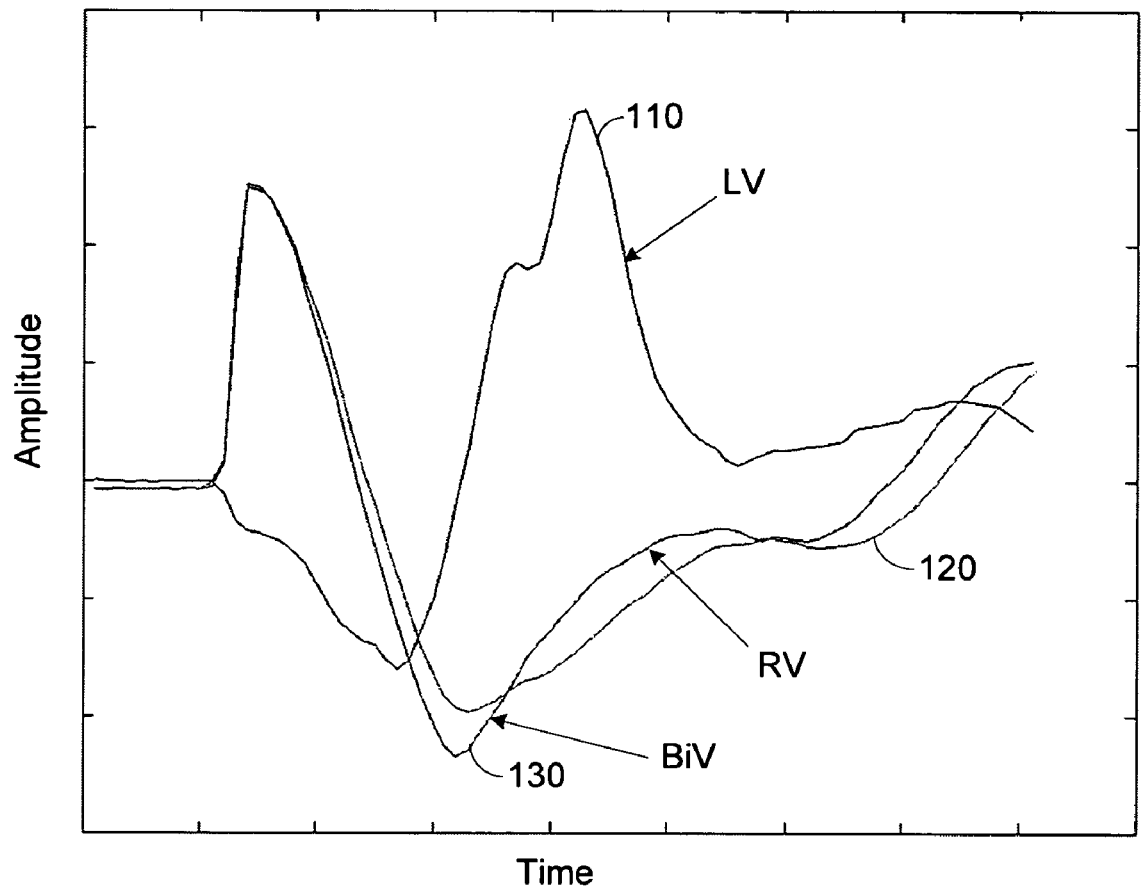
FIG. 1 illustrates cardiac response waveforms for right ventricular capture, left ventricular capture, and biventricular capture that may be used for cardiac response determination in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMETS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Determination of the cardiac response to pacing may be implemented by a pacemaker or other cardiac rhythm management (CRM) device. For example, the cardiac response to a delivered pacing pulse may be determined by a CRM device during capture threshold testing and/or beat-to-beat capture verification. The cardiac pacing responses of one or more heart chambers may be determined based on features of a cardiac signal sensed following delivery of pacing, including single or multi-chamber pacing. More specifically, the cardiac pacing response of one chamber or any combination of the right atrium, left atrium, right ventricle, and left ventricle may be determined. For example, a CRM device may determine the bi-atrial or bi-ventricular pacing response.

During multi-chamber or multi-site pacing, the activation signal sensed at one chamber or site may be altered by the depolarization wavefront initiated at another chamber or site. For example, in bi-ventricular pacing, the signal sensed at the right ventricular coil is primarily influenced by the depolarization wavefront initiated by the right ventricular pace, but is also influenced by the depolarization wavefront initiated by the left ventricular pace. The morphology of the sensed signal may be altered by adjusting the pacing interval between delivery of the left and right pacing pulses. More specifically, for bi-ventricular pacing with a left ventricular (LV) pace delivered first and a right ventricular (RV) pace delivered second, the signal sensed at the right ventricle may be altered by adjusting the interventricular delay (IVD) between the left and right paces.

Multi-chamber or multi-site pacing where natural cross-conduction paths exist provides an opportunity for the activation signal to be altered by the timing between pacing or captured responses of the different paced sites. The present invention involves adjusting relative stimulus times between cardiac chambers or cardiac pacing sites to enhance cardiac pacing response determination. For example, adjusting relative stimulus times to enhance cardiac response determination may involve adjusting the pacing interval between left and right ventricular paces, between left and right atrial paces, between atrial and ventricular pacing, and/or between first and second cardiac sites within an atrium or ventricle.

Sensing cardiac electrical signals following pacing for pacing response determination may employ various combinations of intracardiac or extracardiac electrodes disposed in, on, or around the heart and electrically coupled to the cardiac tissue. In some implementations, electrodes used to deliver a pace to a heart chamber are also used to sense the cardiac signal following pacing. In other implementations, a first combination of electrodes may be used for pacing and a second combination of electrodes may be used for sensing. Spatial separation between the pacing site and the electrode or electrodes used to sense the cardiac signal following pacing facilitate dissipation of the pacing artifact from the sensed signal. Additionally, sensing at an electrode remote from the pacing vector may allow increased flexibility for modifying the signal waveform via adjustment of a pacing interval.

In various implementations, alteration of the activation signal may be accomplished for a pace-sense electrode configuration where the sense vector is sufficiently distant from at least one of the pacing sites and the sense electrode is not one of the cathode electrodes of the pace vector or the sensed signal is not influenced by the pacing artifact. This concept can be used in any combination of electrodes in which there exist two or more distinct pacing sites, and two or more distinct sensing sites. Examples include altering the timing between right atrial (RA) and right ventricular (RV) pacing, right atrial (RA) and left atrial (LA) pacing, LA and RA pacing, right ventricular (RV) and left ventricular (LV) pacing, LV and RV pacing, first LV site and second LV site pacing, and first RV site and second RV site pacing as well as other pacing combinations.

One example of a pacing/sensing electrode combination that facilitates alteration of the activation signal involves sensing for the captured response with the LV proximal electrode referenced to the Can. The LV proximal electrode to Can sensing vector is primarily influenced by LV pacing delivered using the LV distal electrode to LV proximal electrode vector, LV distal electrode to RV coil electrode vector, or LV distal electrode to Can vector, but may also be influenced by RV pacing. In another example, the role of the LV distal and LV proximal electrodes as described immediately above may be interchanged. Additional examples include bi-atrial pacing using the RA ring electrode for sensing or bi-atrial pacing using the LA ring electrode for sensing.

In some embodiments, the right ventricular shock electrode, e.g., RV coil, may be used to sense cardiac signals for determination of left ventricular (LV), right ventricular (RV) and/or bi-ventricular (BiV) pacing responses. Various cardiac responses to pacing are associated with relatively consistent waveform morphologies when sensed using the RV shock electrode. The consistent morphology of the waveforms promotes discrimination of cardiac pacing responses. However, the signal obtained from the RV shock electrode following simultaneous pacing at the LV and RV sites is heavily dominated by the signal components associated with RV activation. FIG. 1 shows superimposed graphs illustrating a waveform representative of LV capture 110, a waveform representative of RV capture 120 and a waveform representative of BiV capture 130 sensed using an RV coil electrode. As can be seen from FIG. 1, the ability to discriminate between RV and BiV capture is limited by a small difference between the respective evoked response signals.

Figure 2:
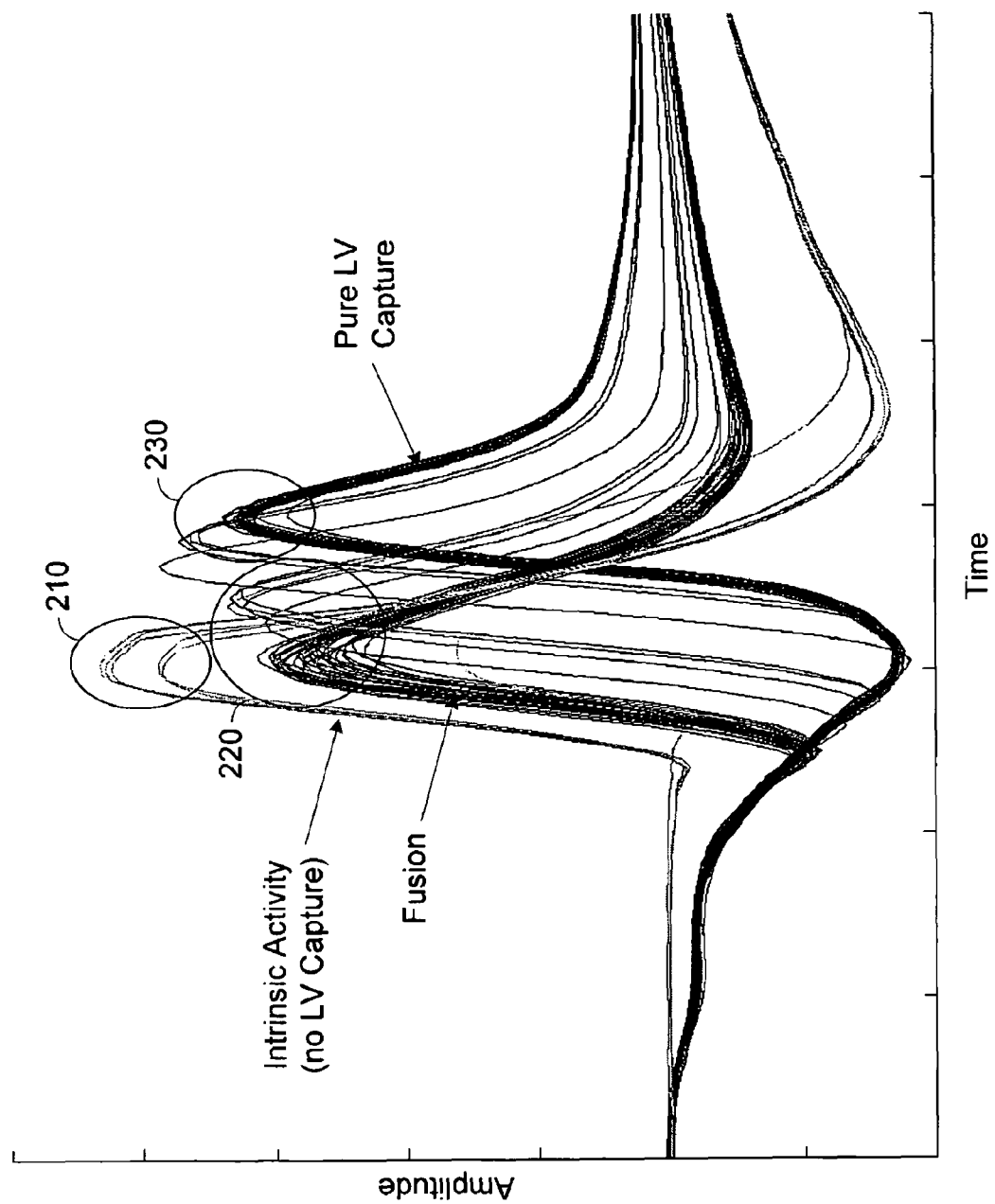
FIG. 2 illustrates cardiac signals associated with left ventricular capture, intrinsic left ventricular depolarization and fusion.

In addition, the conduction time between LV pacing and the arrival of the left depolarization wavefront at the right ventricular electrode complicates cardiac pacing response discrimination due to increased presence of fusion beats. FIG. 2 shows example RV shock channel electrograms recorded during LV pacing. The signals show that signal morphology is dependent on the relative timing of the LV excitation and intrinsic activation.

The superimposed graphs of FIG. 2 include a group of waveforms representative of intrinsic ventricular activity 210; a group of waveforms representative of left ventricular capture 230 and a group of waveforms representative of a fusion response 220. The superimposed graphs of FIG. 2 show the differences in the morphology, e.g., timing and amplitudes of signal peaks, associated with various types of left ventricular pacing responses.

During biventricular pacing, intrinsic and/or LV activated wavefronts sensed on the RV shock electrode produce a signal that includes signal components from LV and/or RV activations, e.g., intrinsic and/or evoked activations. These signal components are dependent on variations in the activation sequence intervals, i.e., AVD and/or IVD. Thus, the morphology of the cardiac signal sensed on the RV shock electrode may vary based on the interventricular delay (IVD) and/or the atrioventricular delay (AVD).

Figure 3B:
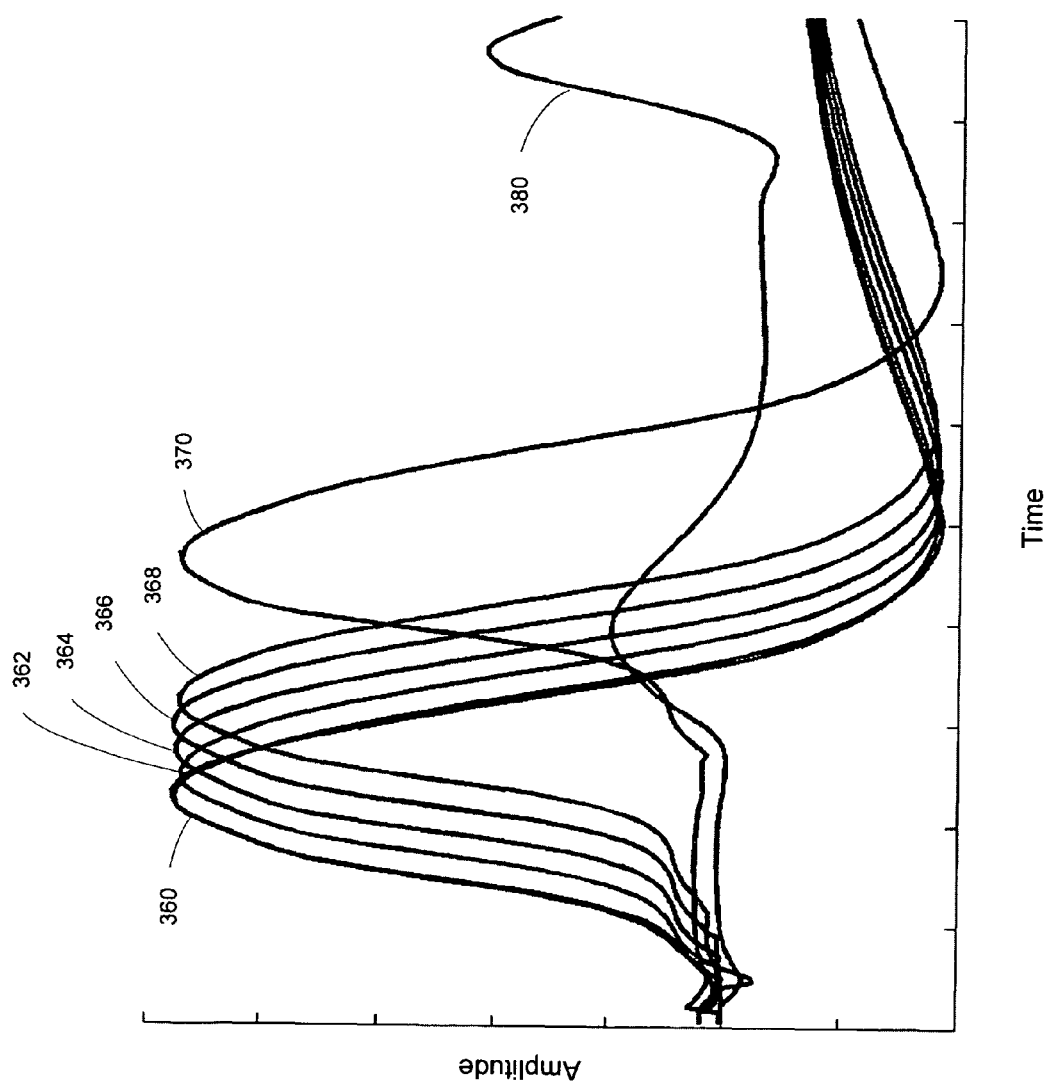
FIG. 3B shows cardiac signals corresponding to right ventricular capture and left ventricular non-capture for biventricular pacing with various interventricular delays as sensed from the right ventricular shock channel in accordance with embodiments of the invention.

FIGS. 3A and 3B illustrate waveforms representative of BiV capture and RV capture for a set AVD and various IVD intervals where in this case AVD is defined as the time delay between RA activation and the first ventricular activation. FIG. 3A is a graph of cardiac signals corresponding to BiV cardiac capture as sensed from the right ventricular shock channel in accordance with embodiments of the present invention. A trace 310 corresponds to the cardiac response to BiV pacing with a 0 millisecond IVD. A trace 312 corresponds to the cardiac response to BiV pacing with a −5 ms IVD. A −5 ms IVD is achieved by delivering the RV pace 5 ms after delivery of the LV pace. Similarly, traces 314, 316, 318, 319, and 320 correspond to the cardiac response to BiV pacing with IVDs of −10 ms, −15 ms, −25 ms, −50 ms, and −75 ms, respectively. Trace 321 corresponds to left ventricular capture only. In this example, the AVD was constant at 25 ms (swine model) between the right atrial activation and the first (left) ventricular pace for each cardiac cycle, and the right ventricular pace then follows the left ventricular pace by −IVD. The AVD in this example is used to promote pacing and avoid fusion due to intrinsic AV conduction & related ventricular activity. As the natural conduction paths to both ventricles originate in the right atrium, and it propagates differently than paced conduction, varying the AVD can change the timing and location of interactions between intrinsic and paced conduction in either ventricle, especially if the AVD is set near a natural conduction time; this variation in the ventricular activation will alter the response signal morphology.

If the AV delay was altered, it would introduce another family of curves for the same range of VV delay. Thus, the shock channel signal morphology represents the interaction of 3 distinct propagating wavefronts which can be controlled by changing the AVD and IVD, all of which can be altered in order to create an optimal capture waveform for discrimination.

The traces 310, 312, 314, 316, 318, 319, and 320 are all representative of BiV captured responses at various IVD values. As can be seen from the superimposed traces, the peak timing and peak amplitude of the BiV captured response shifts as IVD increases in magnitude. Trace 321, which corresponds to LV only capture, is not easily discriminated from traces 319 and 320 illustrating BiV captured responses at IVD=−50 ms and IVD=−75 ms, respectively. As can be seen from this example, discrimination of BiV capture from LV capture may be enhanced by shortening the IVD from about −50 ms.

FIG. 3B shows superimposed graphs of cardiac signals corresponding to BiV pacing with RV capture only (LV noncapture) as sensed from the RV shock channel. The signal sensed on the RV shock channel shows a consistent waveform shifted in time by the relative IVD as the plot timing is referenced from the LV pace.

Traces 360, 362, 364, 366, 368, and 370 correspond to RV capture only for BiV pacing with IVDs of 0 ms, −5 ms, −10 ms, −15 ms, −20 ms, and −50 ms. Trace 380 corresponds to LV only capture. The traces 360, 362, 364, 366, 368 and 370 are all RV shock channel responses for BiV pacing indicating loss of LV capture. As previously discussed, upon loss of LV capture, the RV shock channel signal shows a consistent waveform shifted in time by the relative IVD. No significant decrease in amplitude is observed. The consistency, or inconsistency, of the signal with respect to changes in the IVD may be used in accordance with the present invention to discriminate various responses to pacing as described herein. For example, the IVD may be adjusted to enhance discrimination between BiV capture and RV capture only (LV loss of capture), and/or to enhance discrimination between BiV capture and LV capture only (RV loss of capture).

Figure 4:
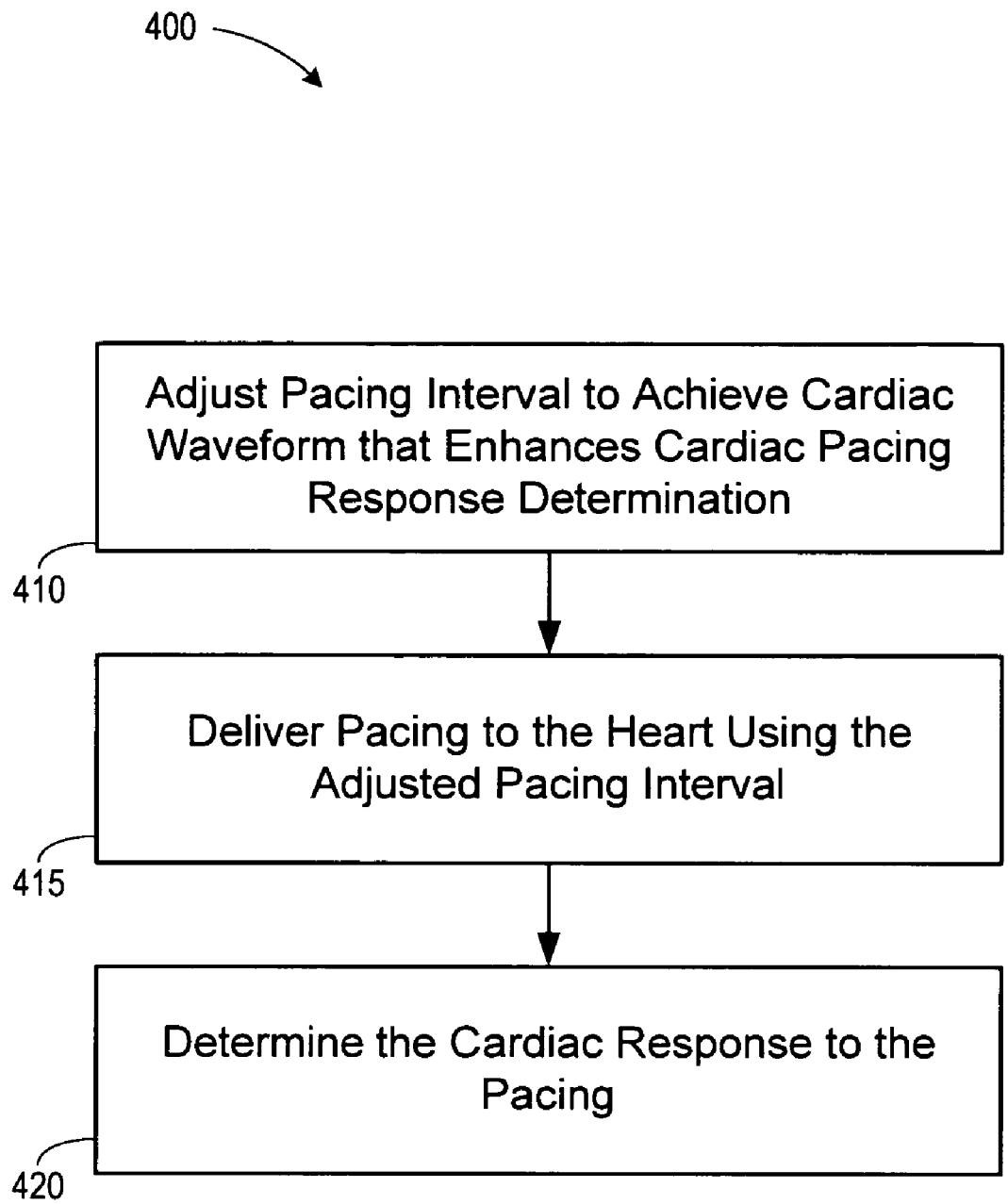
FIG. 4 is a flowchart of a method of determining a cardiac pacing response using adjusted pacing intervals in accordance with embodiments of the invention.

FIG. 4 is a flowchart of a method 400 for determining the cardiac response to pacing in accordance with embodiments of the invention. A pacing interval, e.g., IVD or AV, is adjusted 410 to achieve a cardiac waveform that enhances determination of the cardiac pacing response. Pacing is delivered 415 to the heart using the adjusted pacing interval. The cardiac response to the pacing is determined 420.

For example, in a swine model, as illustrated in FIGS. 3A and 3B, the IVD may be adjusted to achieve a waveform suitable or optimal for the particular types of pacing responses that are being distinguished. In this example, BiV capture may be more easily discriminated from RV capture only using an IVD longer than −25 ms such that the LV pace precedes the RV pace by 25 ms or more.

Pacing interval adjustment to enhance cardiac pacing response determination may be particularly useful when implemented in connection with a capture threshold test. Other scenarios where the pacing interval adjustment approaches of the present invention may be advantageously employed include beat-to-beat capture verification, during fusion/noise management processes, and/or to adapt to changing patient dynamics such as temporal changes in the capture waveform morphology. In one implementation, the pacing interval may be adjusted to achieve a cardiac pacing response waveform morphology that enhances cardiac pacing response determination in the presence of fusion or noise. Fusion management processes that may be adapted to use an adjusted pacing interval as described in the embodiments presented herein are discussed in commonly owned U.S. Patent Publication No. 20060247693, which is incorporated herein by reference.

Figure 5A:
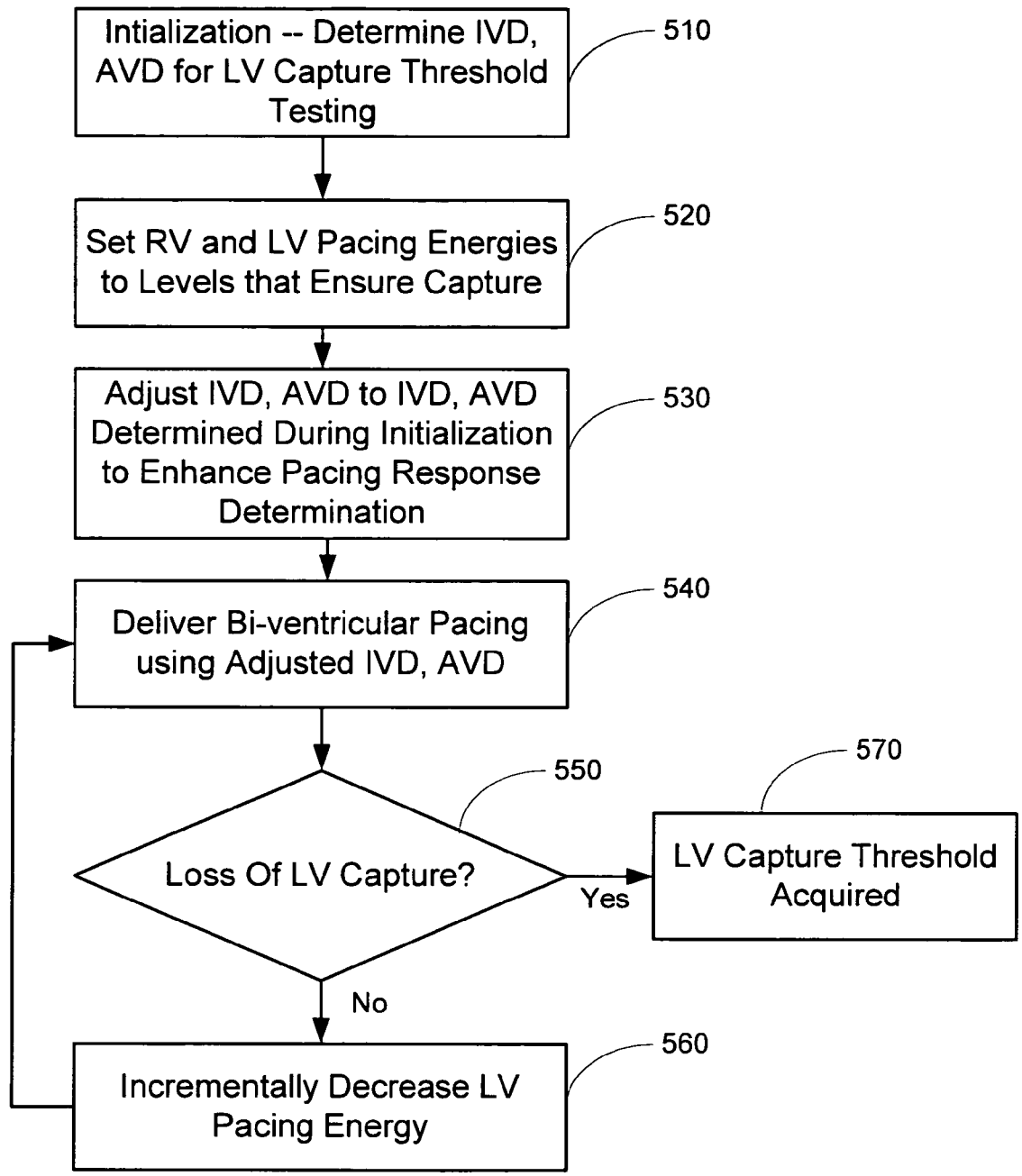
FIGS. 5A-5C are flowcharts illustrating methods for performing capture threshold testing in accordance with embodiments of the invention.

FIG. 5A illustrates a flowchart of a method that may be used to adjust pacing intervals used during capture threshold testing. In this particular example, the IVD is adjusted for LV capture threshold testing. In other implementations, one or more pacing intervals may be adjusted to achieve a waveform suitable for performing an RV capture threshold test, or left or right atrial capture threshold tests.

In the example illustrated by the flowchart of FIG. 5A, prior to the start of capture threshold testing, an IVD and/or an AVD suitable for LV capture threshold testing is determined 510 during an initialization process. The IVD and/or AVD determined during the initialization process allow the system to more easily distinguish between BiV capture and LV loss of capture (RV capture only) As can be seen from FIGS. 3A and 3B, the waveforms representative of BiV capture (FIG. 3A) and RV only capture (FIG. 3B) may have a similar morphology. Adjustment of the IVD and/or AVD enhances the ability to distinguish between these types of cardiac pacing responses.

Figure 5B:
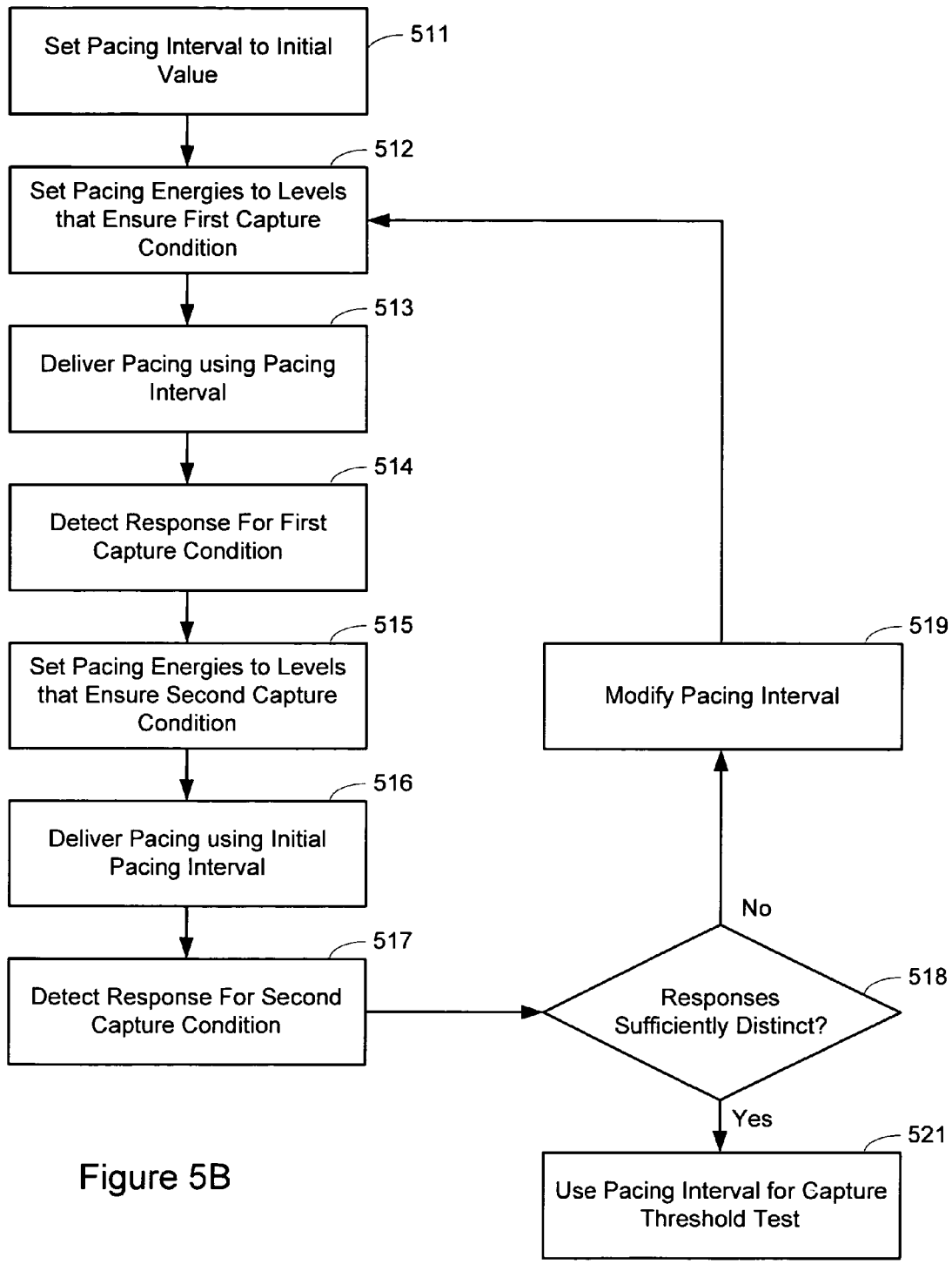
Figure 5C:
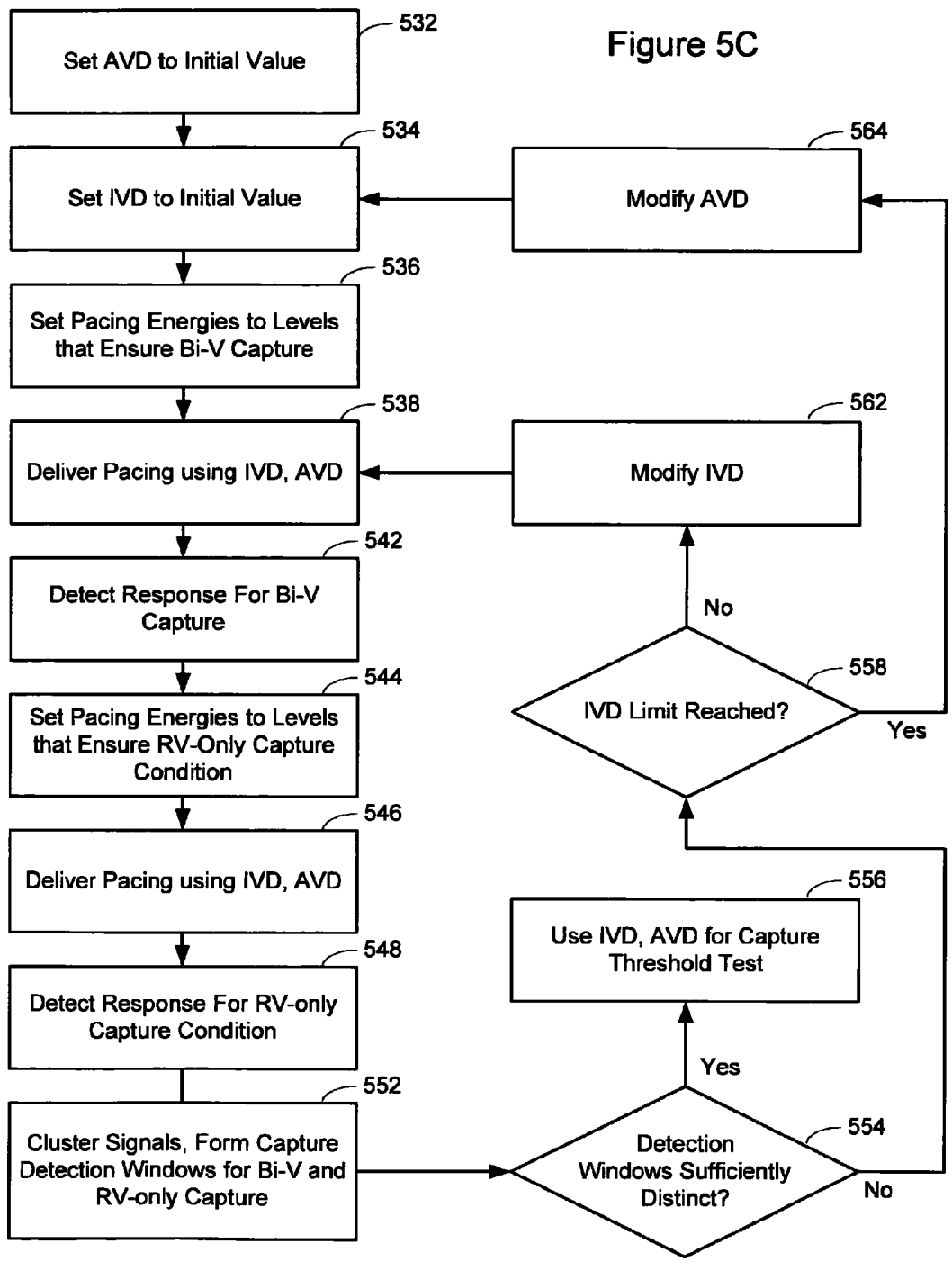

FIGS. 5B and 5C are flowcharts illustrating examples of the initialization process in accordance with embodiments of the invention. FIG. 5B illustrates the initialization process if only one pacing interval is adjusted. FIG. 5C illustrates the initialization process if two pacing intervals, IVD and AVD, are adjusted. The initialization process may not need to be performed for each capture threshold test. In some embodiments, after the pacing interval(s), e.g., AVD and/or IVD, are determined in a first capture threshold test, the pacing interval(s) may be reconfirmed during subsequent capture threshold tests. For example, determination of the pacing interval(s) may be initiated only when there are no previously determined pacing interval(s) or the previously determined pacing interval(s) are no longer producing captured response signals that are sufficiently distinct for capture response determination.

In FIG. 5B the pacing interval to be adjusted is set 511 to an initial value. The pacing energies are set 512 to values that ensure a first capture condition, e.g., BiV capture, and pacing is delivered 513. The response to pacing for the first capture condition is detected 514. The pacing energies are set 515 to ensure a second capture condition, e.g., RV only capture, and pacing is delivered 516. The response to pacing for the second capture condition is detected 517.

If the responses for the first capture condition and the second capture condition are sufficiently distinct 518, allowing the two capture conditions to be discriminated, then the pacing interval is used 521 for the capture threshold test. If the responses for the first capture condition and the second capture condition are not sufficiently distinct 518, then the pacing interval is modified 519 and initialization continues as described in blocks 512-518. The pacing interval that produces a first capture condition response that is sufficiently distinct from the second capture condition response is used 521 for the capture threshold test.

FIG. 5C is a flowchart illustrating the initialization process when both the AVD and IVD are adjusted to enhance discrimination between BiV and RV only capture in accordance with embodiments of the invention. The AVD and IVD are set 532, 534 to their respective initial values. The pacing energies are set 536 to levels that ensure capture of both the left and the right ventricles and pacing is delivered 538 using the AVD and IVD. The signal responses for BiV capture are detected 542. The pacing energies are set 544 to levels that ensure capture of the RV and non-capture of the LV (RV only capture) and pacing is delivered 546 using the AVD and IVD. The signal responses for RV only capture are detected 548.

The signal responses for the two types of capture conditions are clustered and capture detection windows are formed 552 from the clusters. For example, clustering and capture detection window formation may be accomplished, for example, using processes described in commonly owned U.S. Pat. No. 7,499,751, which is incorporated herein by reference. If the capture detection windows are sufficiently distinct 554, then the IVD and AVD are used 556 for the capture threshold test. If the capture detection windows are not sufficiently distinct 554, then the IVD may be adjusted 562 by an incremental amount, unless an IVD limit has been reached 558. If the IVD limit has been reached 558, then the AVD may be adjusted, the IVD set to the initial value, and the initialization continues as described in blocks 534-562. The AVD and IVD intervals that produce a BiV captured response that is sufficiently distinct from the RV-only captured response is used 556 for the capture threshold test.

Returning to FIG. 5A, after the initialization process is completed 510, the RV and LV pacing energies are initially set 520 to a level that ensures capture of both ventricles. The IVD and/or AVD are adjusted 530 to the values determined during the initialization process and BiV pacing is delivered 540. The LV pacing energy is decreased 560 in discrete steps until LV loss of capture (RV only capture) is detected 550. The energy level at which LV capture is lost, e.g. the energy level the results in LV non-capture for 3 out of 5 paces, is determined to be 570 the LV capture threshold for BiV pacing.

Determination of the cardiac pacing response may involve analyzing signal features of the cardiac signal produced following delivery of pacing. Cardiac pacing response determination based on signal features relies on the consistency of the waveforms representative of various types of pacing responses. For example, cardiac pacing response determination may use templates of the heart's pacing response signal as the basis for determining whether pacing produces a particular type of pacing response. Templates representative of various types of cardiac pacing responses may comprise one or more detection windows that are defined in terms of an amplitude range and a time range. The detection windows are used to analyze a cardiac signal sensed following delivery of multi-chamber pacing. Whether or not the cardiac signal falls within the amplitude and time ranges of the detection windows may be used to determine the cardiac pacing response.

As illustrated in the example illustrated by FIG. 5A, adjustment of the IVD may be used to enhance LV capture threshold testing. As previously described, the RV shock electrode may be used for evoked response sensing. In some cases, the time between delivery of the pace in the LV and sensing the propagated LV signal on the RV electrode can be in excess of 100 ms. The length of the delay between pacing the LV and sensing the propagated LV signal may prevent the delivery of a backup pace in the event of loss of capture. But, because bi-ventricular pacing is delivered with a pacing stimulus to the right ventricle at a level sufficient to stimulate, continuous ventricular rate support is ensured. To generate an evoked response signal that reflects a significant contribution from the LV activation, (i.e., LV capture), the LV site is paced prior to pacing the RV site. The IVD is adjusted to allow the LV activation to alter the cardiac signal sensed at the RV electrode so that the signal reflects a significant signal change when LV capture is lost. This method could be extended to any multi-site pacing scheme in which the local signal, which may be affected primarily by the locally generated wavefront, can be altered by the timing of depolarization wavefronts originating at remote sites. The method may also be used to detect capture of a remote site in the presence of intrinsic activation at the local site where sensing occurs, providing stable AV conduction is present.

In the case of LV pacing threshold detection during BiV pacing at a given IVD, the detection scheme can be used to detect LV loss of capture by sensing in the RV for a signal exhibiting RV capture only (LV loss of capture) morphology. The consistency of the LV loss of capture morphology as opposed to the BiV capture signal morphology would allow for an effective method of discriminating between BiV capture and RV only capture (LV loss of capture).

Figure 6A:
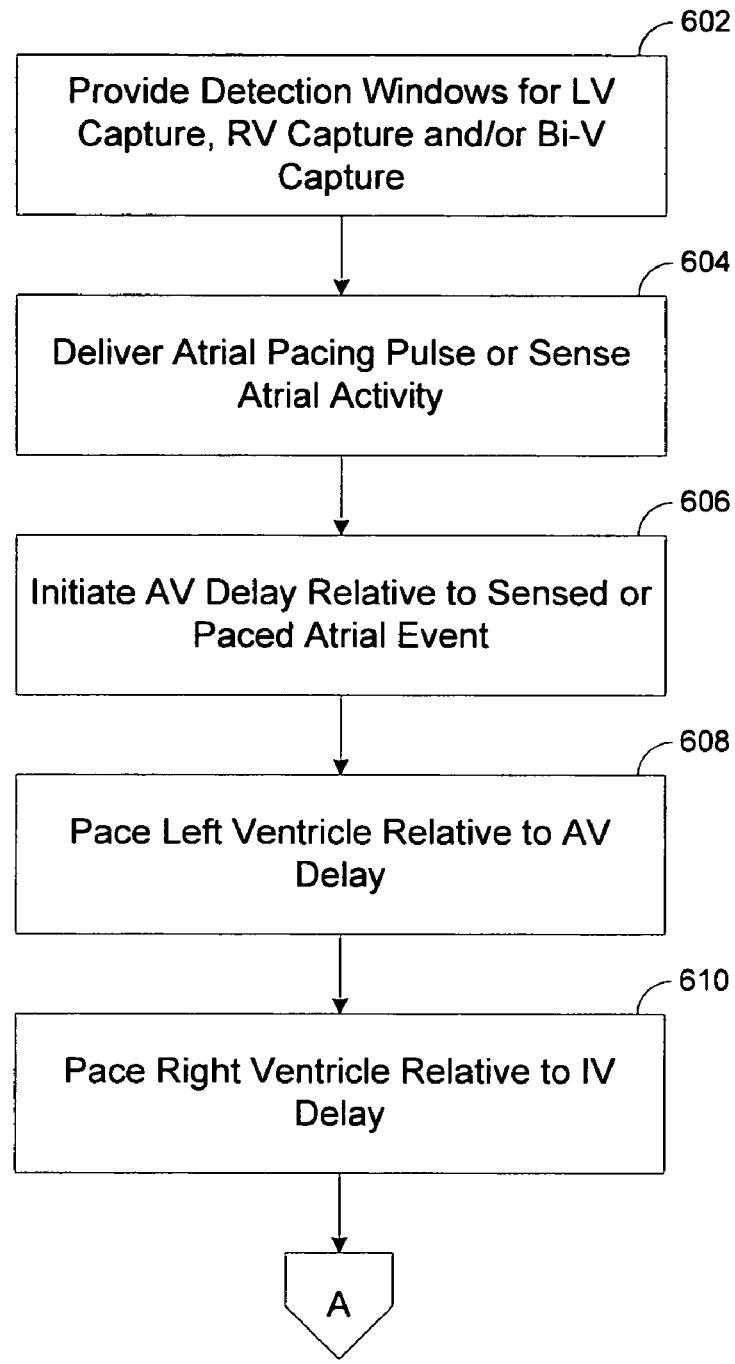
FIGS. 6A and 6B are flowcharts of a method of detecting capture for biventricular pacing in accordance with embodiments of the invention.
Figure 6B:
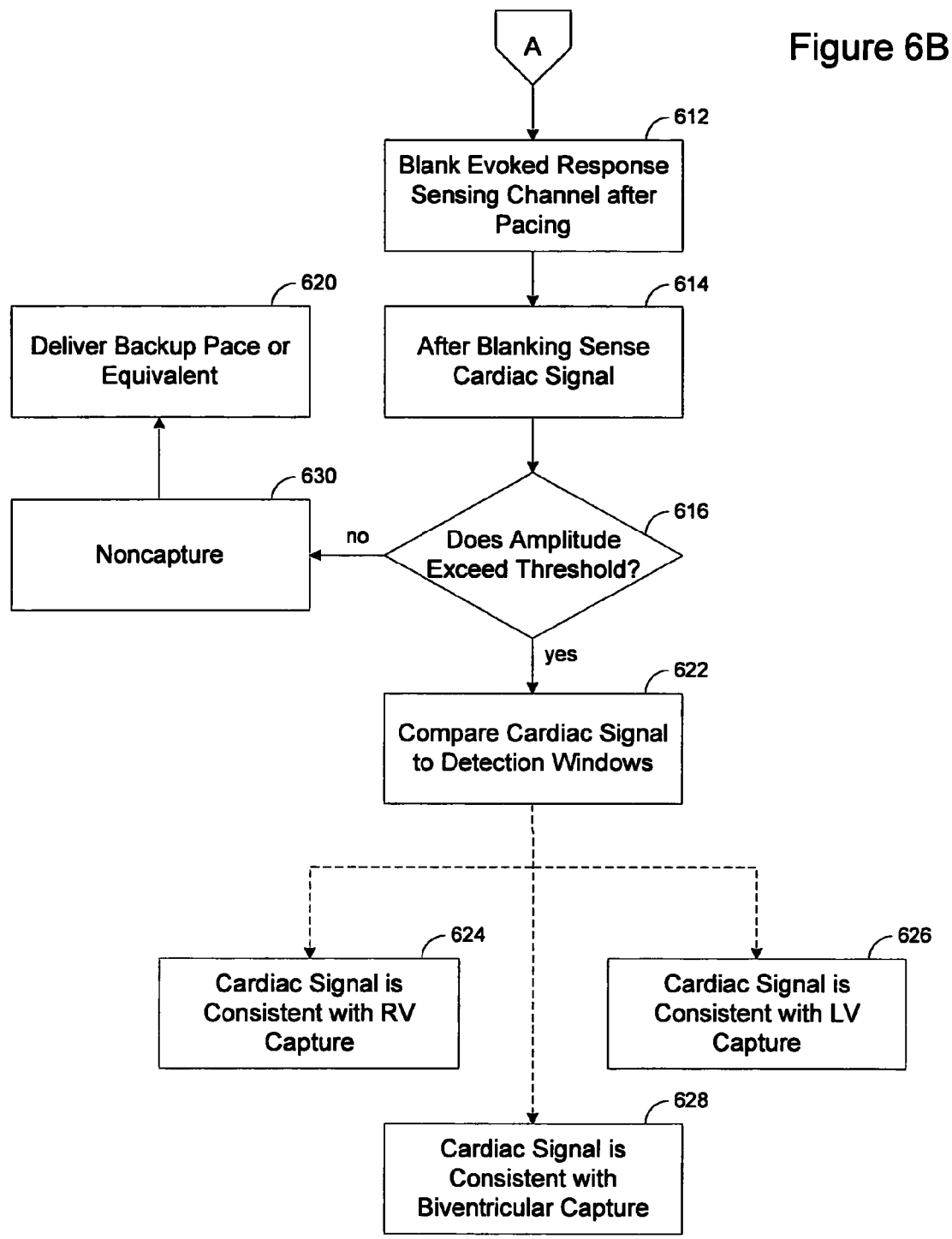

FIGS. 6A and 6B illustrate a flowchart of a multi-chamber capture detection method in accordance with the present invention as applied to a BiV pacing embodiment. Capture detection for BiV pacing, aspects of which may be utilized in conjunction with pacing interval adjustment as described herein, are discussed in commonly owned U.S. Pat. No. 7,392,088, which is incorporated herein by reference.

Detection windows are provided 602, each detection window corresponding to an expected feature of the cardiac signal under conditions of LV capture, RV capture or BiV capture. The detection windows may be defined in terms of amplitude and time ranges. The detection windows can be provided based on clinical data taken from a number of patients or may be formed based on data taken from the patient.

In one implementation, detection windows associated with a particular capture condition may be formed by measuring a number of cardiac signals of the patient under the particular capture condition, extracting one or more features from each of the cardiac signals, clustering the features, and determining detection window boundaries based on the clustered features. In one implementation, the features extracted and clustered comprise positive and negative cardiac signal peaks. Forming detection windows based on clustering is described in commonly owned U.S. patent application Ser. No. 11/116,544 previously incorporated herein by reference. The one or more detection windows used for detecting the particular capture condition form a detection template. Detection windows and templates comprising one or more detection windows for each capture condition (LV capture, RV capture, and bi-ventricular capture) may be formed using the clustering approach or other methods.

During a cardiac cycle, an atrial pacing pulse is delivered to the atrium or atrial activity is sensed 604. An AV delay is initiated 606 relative to the sensed or paced atrial event. The left ventricle is paced 608 relative to the AV delay and the right ventricle is paced 610 relative to an IVD. The length of the IVD produces a waveform morphology that enhances pacing response determination.

The sensing channel used for capture detection, e.g., an evoked response sensing channel, is blanked 612 after each ventricular pace. For example, the evoked response channel may be blanked for a period of time during the IVD and for about 0 milliseconds to about 40 milliseconds after the last ventricular pace. After blanking, the cardiac signal is sensed 614. The cardiac signal comprises a cardiac electrogram signal that may be sensed using one or more electrodes positioned within one or more heart chambers and/or within one or more veins of the heart. In various implementations, the cardiac electrogram signal maybe sensed using an electrode positioned in the right ventricle (RV tip electrode, RV ring electrode or RV coil electrode), an electrode positioned within a vein of the left ventricle (LV distal electrode or LV proximal electrode), and/or electrodes positioned in the right atrium and the left atrium vein, for example. For example, in one embodiment, the cardiac electrogram signal is sensed using the RV coil to can sensing vector.

The cardiac signal is compared to an activity detection threshold (ADT) which comprises positive and negative thresholds. If the cardiac signal does not exceed 616 the ADT in either the positive or negative direction, then the cardiac response is determined 618 to be a non-captured response (neither chamber captured). If non-capture is detected, 618 a back up pace or equivalent, as discussed earlier, may be delivered 620 to one or both ventricles.

If the cardiac signal exceeds 616 the ADT, the cardiac signal morphology is compared to the expected morphology associated with various capture conditions. Cardiac signal features are extracted and compared to detection windows comprising a template associated with a particular type of capture condition. Cardiac signal features may be compared 622 to one or more of a template associated with bi-ventricular capture, a template associated with LV capture and a template associated with RV capture.

In one implementation, the extracted features of the cardiac signal may comprise positive and negative peaks. The amplitude and timing of the cardiac signal peaks may be compared to expected peak amplitudes and peak times associated with capture conditions LV capture, RV capture, and/or bi-ventricular capture.

If the cardiac signal peaks fall within one or more detection windows associated with LV capture, then the capture condition is determined 626 to be LV capture. If the cardiac signal peaks fall within one or more detection windows associated with RV capture, then the capture condition is determined 624 to be RV capture. If the cardiac signal peaks fall within one or more detection windows associated with bi-ventricular capture, then the capture condition is determined 628 to be bi-ventricular capture. If the cardiac signal peaks do not fall within any of the detection windows, or if the cardiac signal peaks fall within multiple detection windows representing different capture conditions, then the capture condition may be determined to be fusion.

Figure 7A:
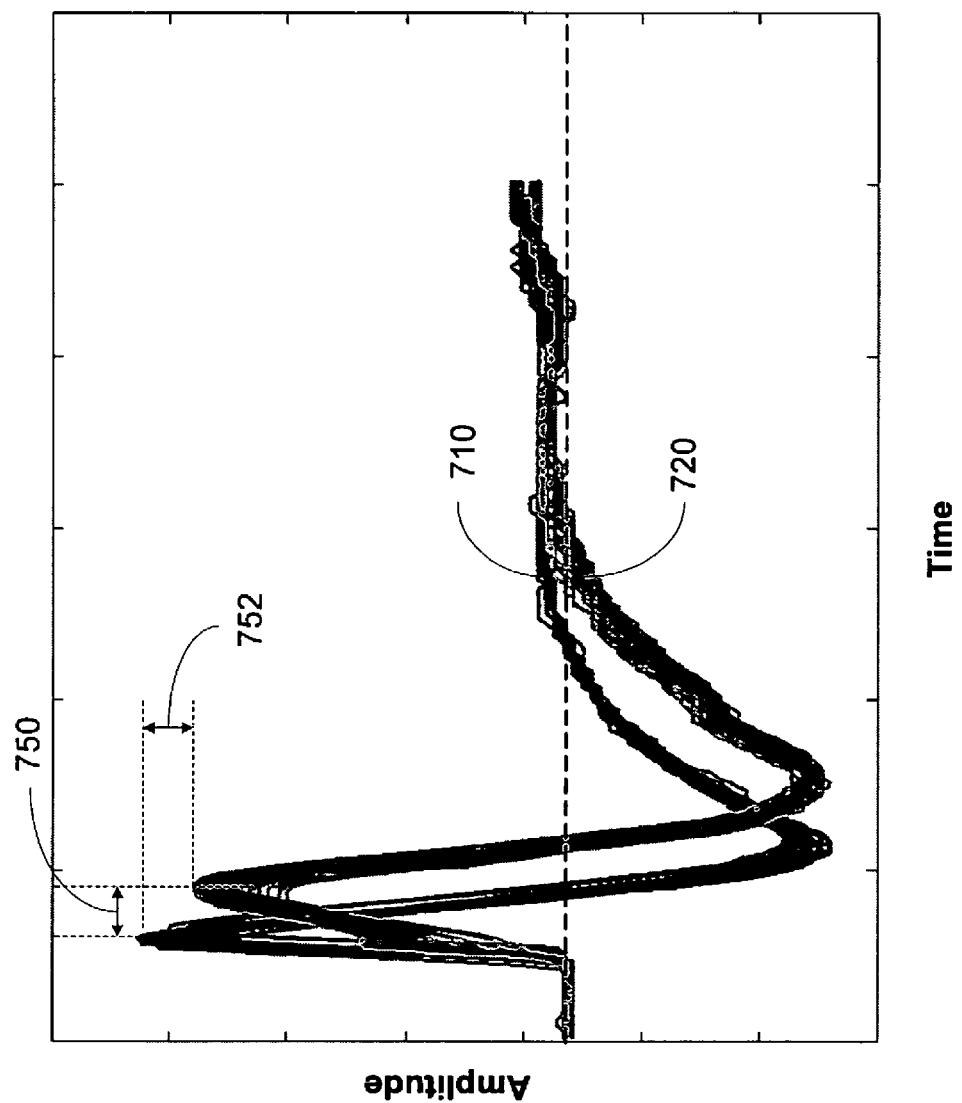
FIG. 7A illustrates changes in a morphological waveform feature that may be used to discriminate between a first type of cardiac pacing response and a second type of cardiac pacing response in accordance with embodiments of the invention.

FIG. 7A shows superimposed graphs of waveforms representative of BiV capture 710 and superimposed graphs of waveforms representative of RV only capture 720. In this example, adjusting the IVD provides a peak timing shift of the cardiac waveform of approximately 40 ms 750 between RV only capture 720 (LV non-capture) and BiV capture 710 and/or may shift the peak amplitude of the cardiac waveform by an amount of 2 mV or more 752. The negative peak of the cardiac waveform, as well as other waveform features, may also be shifted by increasing or decreasing the IVD.

Figure 7B:
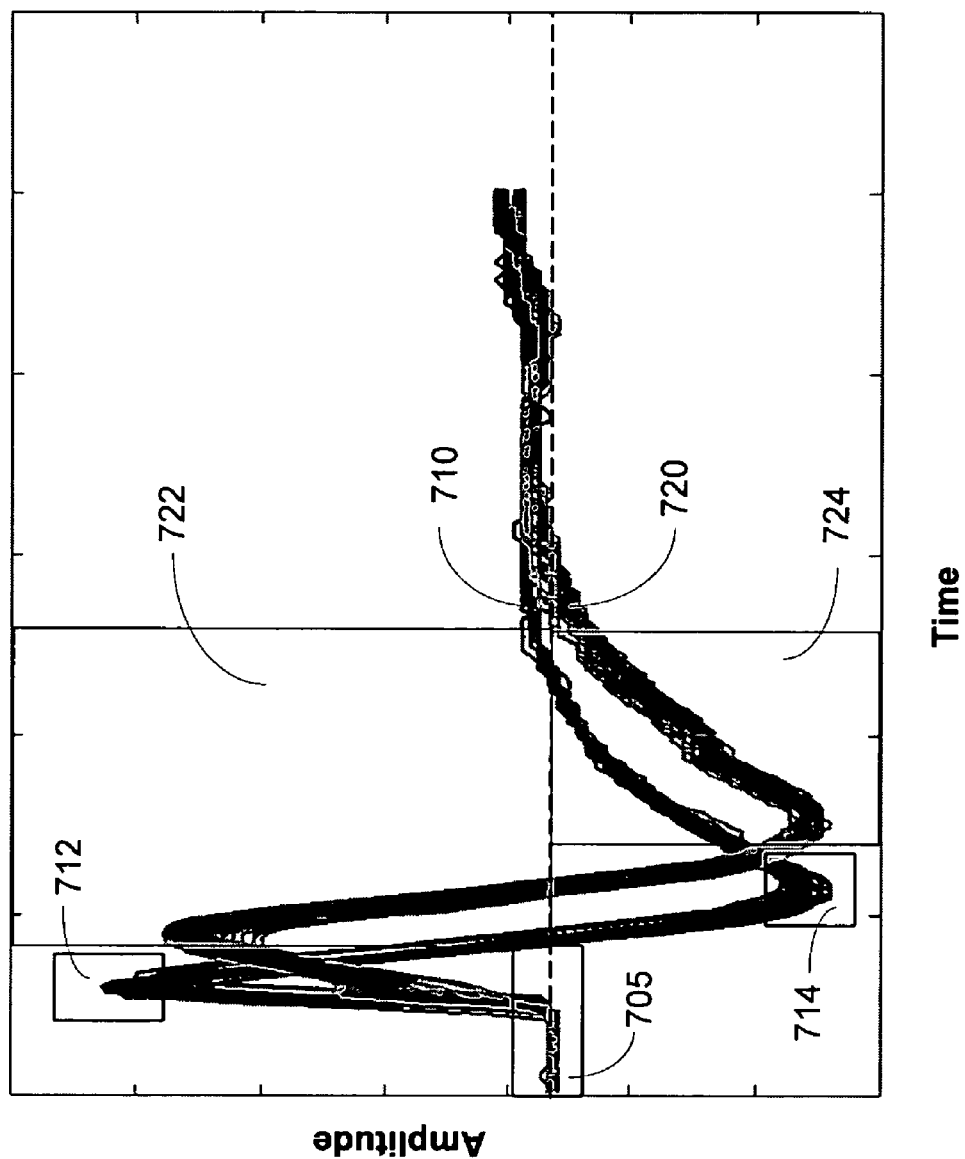
FIG. 7B illustrates detection windows that may be used for cardiac response determination in accordance with embodiments of the invention.

FIG. 7B illustrates detection windows that may be used to detect LV loss of capture in accordance with embodiments of the invention. FIG. 7B shows superimposed graphs of signals representative of bi-ventricular capture 710 and superimposed graphs of signals representative of RV capture only (LV non-capture) 720. These signals are sensed following pacing pulses delivered to the left and right ventricles with an IVD adjusted to a value suitable for cardiac pacing response determination in accordance with embodiments of the invention. A signal similar to the composite bi-ventricular capture waveform 710 is produced when the pacing pulses capture both ventricles. A signal similar to the composite RV capture waveform 720 is produced when the pacing pulse delivered to the right ventricle captures the right ventricle and the pacing pulse delivered to the left ventricle does not capture the left ventricle.

Both the bi-ventricular capture waveform 710 and the RV capture waveform 720 have an initial peak followed by a peak of opposite polarity. However, the waveforms 710, 720 differ in morphology. As can be seen from FIG. 7, the morphology of the waveform 720 associated with RV only capture has slightly wider peak widths and the peaks are delayed in time when compared to the waveform 710 associated with bi-ventricular capture.

The morphological differences between signals associated with bi-ventricular capture 710 and signals associated with RV capture 720 can be utilized to discriminate between bi-ventricular capture and RV capture (LV non-capture). FIG. 7 illustrates detection windows 712, 714, 722, 724 that may be used to discriminate between bi-ventricular capture and RV capture.

First 712 and second 714 bi-ventricular detection windows are used to detect bi-ventricular capture. If the positive peak of a cardiac signal falls within the first bi-ventricular detection window 712 and the negative peak of the cardiac signal falls within the second bi-ventricular detection window 714, then the system determines that both the left and the right ventricles were captured by the pacing pulses.

If the positive peak of the cardiac signal falls in the first RV capture detection window 722 and the negative peak of the cardiac signal falls in the second RV capture detection window 724, then the system determines that the pacing pulse delivered to the right ventricle captured the right ventricle and the pacing pulse delivered to the left ventricle did not capture the left ventricle. If the positive or negative value of the cardiac signal does not exceed the ADT 705, then neither ventricle was captured. If the cardiac signal peaks do not fall within any of the detection windows, or if the cardiac signal peaks fall within multiple detection windows representing the two capture conditions, then the capture condition may be determined to be fusion.

The embodiments of the present system illustrated herein are generally described as being implemented in a patient implantable medical device such as a pacemaker/defibrillator (PD) that may operate in numerous pacing modes known in the art. Various types of multiple chamber implantable cardiac pacemaker/defibrillators are known in the art and may be used in connection with cardiac devices and methods that provide multi-chamber capture detection using pacing interval adjustment in accordance with the approaches of the present invention. The methods of the present invention may be implemented in a variety of implantable or patient-external cardiac rhythm management devices, including multi-chamber pacemakers, defibrillators, cardioverters, bi-ventricular pacemakers, cardiac resynchronizers, and cardiac monitoring systems, for example.

A device suitable for implementing the cardiac pacing response determination methods of the present invention may include stimulation circuitry for delivering stimulation pulses to the heart and includes sensing circuitry comprising electrodes electrically coupled to the heart. Leads from the sensing and/or stimulation circuitry are coupled to electrodes positioned within heart chambers, positioned within veins of the heart, and/or positioned on the heart. The electrodes sense the heart's electrical signals, which are denoted cardiac electrogram signals. Each lead may include multiple electrodes, and each electrode may be used to sense a separate electrogram signal for capture detection.

Although the present system is described in conjunction with an implantable cardiac pacemaker/defibrillator having a microprocessor-based architecture, it will be understood that the implantable pacemaker/defibrillator (or other device) may be implemented using any logic-based circuit architecture, if desired.

Figure 8:
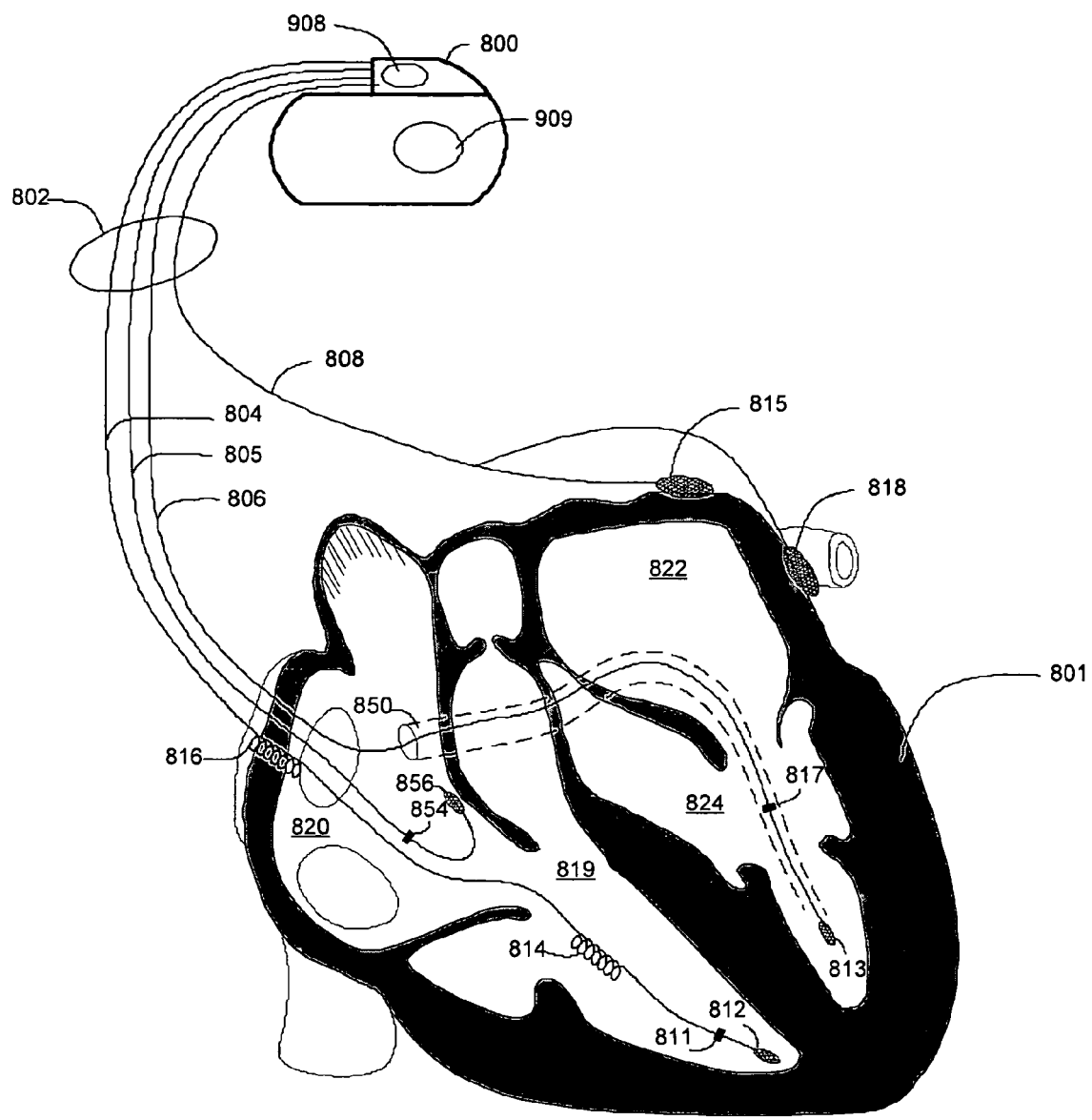
FIG. 8 is a sectional view of a patient's heart incorporating illustrations of an implantable medical device and several possible lead arrangements useful in accordance with embodiments of the present invention.

Referring now to FIG. 8 of the drawings, there is shown a partial view of a cardiac rhythm management device that may be used to implement pacing interval adjustment for cardiac pacing response determination in accordance with the present invention. The cardiac rhythm management device in FIG. 8 includes a pacemaker/defibrillator 800 electrically and physically coupled to a lead system 802. The housing and/or header of the pacemaker/defibrillator 800 may incorporate one or more electrodes 908, 909 used to provide electrical stimulation energy to the heart and to sense cardiac electrical activity. The pacemaker/defibrillator 800 may utilize all or a portion of the pacemaker/defibrillator housing as a can electrode 909. The pacemaker/defibrillator 800 may include an indifferent electrode 908 positioned, for example, on the header or the housing of the pacemaker/defibrillator 800. If the pacemaker/defibrillator 800 includes both a can electrode 909 and an indifferent electrode 908, the electrodes 908, 909 typically are electrically isolated from each other.

The lead system 802 is used to detect electric cardiac signals produced by the heart 801 and to provide electrical energy to the heart 801 under certain predetermined conditions to treat cardiac arrhythmias. The lead system 802 may include one or more electrodes used for pacing, sensing, and/or defibrillation. In the embodiment shown in FIG. 8, the lead system 802 includes an intracardiac right ventricular (RV) lead system 804, an intracardiac right atrial (RA) lead system 805, an intracardiac left ventricular (LV) lead system 806, and an extracardiac left atrial (LA) lead system 808. The lead system 802 of FIG. 8 illustrates one embodiment that may be used in connection with the cardiac pacing response determination methodologies described herein. Other leads and/or electrodes may additionally or alternatively be used.

The lead system 802 may include intracardiac leads 804, 805, 806 implanted in a human body with portions of the intracardiac leads 804, 805, 806 inserted into a heart 801. The intracardiac leads 804, 805, 806 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 8, the lead system 802 may include one or more extracardiac leads 808 having electrodes, e.g., epicardial electrodes, positioned at locations outside the heart for sensing and pacing one or more heart chambers.

The right ventricular lead system 804 illustrated in FIG. 8 includes an SVC-coil 816, an RV-coil 814, an RV-ring electrode 811, and an RV-tip electrode 812. The right ventricular lead system 804 extends through the right atrium 820 and into the right ventricle 819. In particular, the RV-tip electrode 812, RV-ring electrode 811, and RV-coil electrode 814 are positioned at appropriate locations within the right ventricle 819 for sensing and delivering electrical stimulation pulses to the heart 801. The SVC-coil 816 is positioned at an appropriate location within the right atrium chamber 820 of the heart 801 or a major vein leading to the right atrial chamber 820 of the heart 801.

In one configuration, the RV-tip electrode 812 referenced to the can electrode 909 may be used to implement unipolar pacing and/or sensing in the right ventricle 819. Bipolar pacing and/or sensing in the right ventricle may be implemented using the RV-tip 812 and RV-ring 811 electrodes. In yet another configuration, the RV-ring electrode 811 may optionally be omitted, and bipolar pacing and/or sensing may be accomplished using the RV-tip electrode 812 and the RV-coil 814, for example. The RV-coil 814 and the SVC-coil 816 are defibrillation electrodes.

The left ventricular lead 806 includes an LV distal electrode 813 and an LV proximal electrode 817 located at appropriate locations in or about the left ventricle 824 for pacing and/or sensing the left ventricle 824. The left ventricular lead 806 may be guided into the right atrium 820 of the heart via the superior vena cava. From the right atrium 820, the left ventricular lead 806 may be deployed into the coronary sinus ostium, the opening of the coronary sinus 850. The lead 806 may be guided through the coronary sinus 850 to a coronary vein of the left ventricle 824. This vein is used as an access pathway for leads to reach the surfaces of the left ventricle 824 which are not directly accessible from the right side of the heart. Lead placement for the left ventricular lead 806 may be achieved via subclavian vein access and a preformed guiding catheter for insertion of the LV electrodes 813, 817 adjacent to the left ventricle.

Unipolar pacing and/or sensing in the left ventricle may be implemented, for example, using the LV distal electrode referenced to the can electrode 909. The LV distal electrode 813 and the LV proximal electrode 817 may be used together as bipolar sense and/or pace electrodes for the left ventricle. The left ventricular lead 806 and the right ventricular lead 804, in conjunction with the pacemaker/defibrillator 800, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 805 includes a RA-tip electrode 856 and an RA-ring electrode 854 positioned at appropriate locations in the right atrium 820 for sensing and pacing the right atrium 820. In one configuration, the RA-tip 856 referenced to the can electrode 909, for example, may be used to provide unipolar pacing and/or sensing in the right atrium 820. In another configuration, the RA-tip electrode 856 and the RA-ring electrode 854 may be used to provide bipolar pacing and/or sensing.

FIG. 8 illustrates one embodiment of a left atrial lead system 808. In this example, the left atrial lead 808 is implemented as an extracardiac lead with LA distal 818 and LA proximal 815 electrodes positioned at appropriate locations outside the heart 801 for sensing and pacing the left atrium 822. Unipolar pacing and/or sensing of the left atrium may be accomplished, for example, using the LA distal electrode 818 to the can 909 pacing vector. The LA proximal 815 and LA distal 818 electrodes may be used together to implement bipolar pacing and/or sensing of the left atrium 822. The right atrial lead 805 and the left atrial lead 808 may be used in conjunction with the pacemaker/defibrillator 800 to provide bi-atrial pacing.

Figure 9:
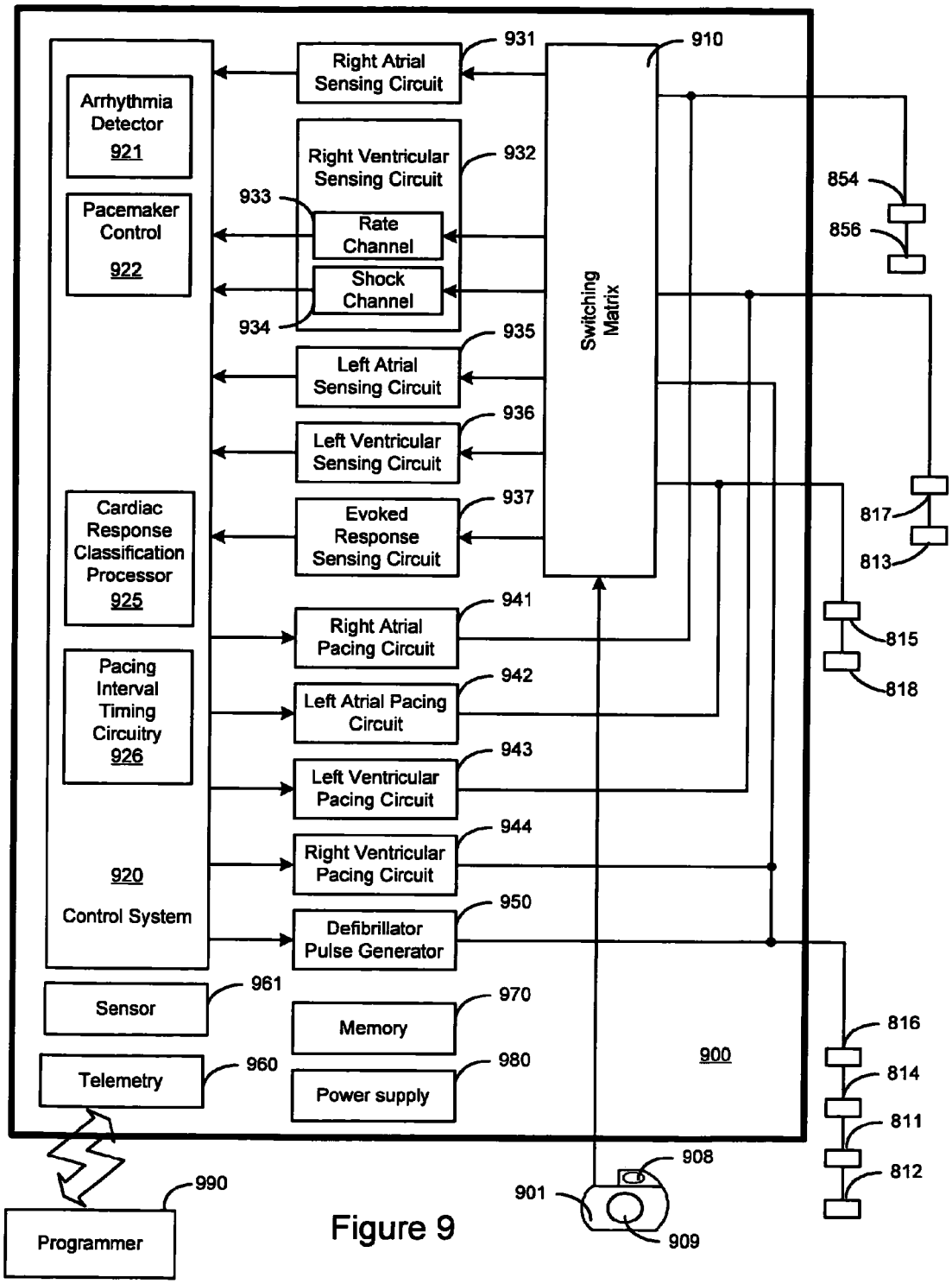
FIG. 9 is a block diagram of an implantable medical device that may be used to implement cardiac response determination using adjusted pacing intervals in accordance with embodiments of the present invention.

Referring now to FIG. 9, there is shown a block diagram of a cardiac pacemaker/defibrillator 900 suitable for implementing adjustment of pacing intervals to achieve a waveform morphology that enhances cardiac pacing response determination. FIG. 9 shows a cardiac pacemaker/defibrillator 900 divided into functional blocks. It is understood by those skilled in the art that there exist many possible configurations in which these functional blocks can be arranged. The example depicted in FIG. 9 is one possible functional arrangement. Other arrangements are also possible. For example, more, fewer or different functional blocks may be used to describe a cardiac pacemaker/defibrillator suitable for implementing the methodologies for multi-chamber capture detection in accordance with the present invention. In addition, although the cardiac pacemaker/defibrillator 900 depicted in FIG. 9 contemplates the use of a programmable microprocessor-based logic circuit, other circuit implementations may be utilized.

The cardiac pacemaker/defibrillator 900 depicted in FIG. 9 includes circuitry for receiving cardiac signals from a heart and delivering electrical stimulation energy to the heart in the form of pacing pulses or defibrillation shocks. In one embodiment, the circuitry of the cardiac pacemaker/defibrillator 900 is encased and hermetically sealed in a housing 901 suitable for implanting in a human body. Power to the cardiac pacemaker/defibrillator 900 is supplied by an electrochemical battery 980. A connector block (not shown) is attached to the housing 901 of the cardiac pacemaker/defibrillator 900 to allow for the physical and electrical attachment of the lead system conductors to the circuitry of the cardiac pacemaker/defibrillator 900.

The cardiac pacemaker/defibrillator 900 may be a programmable microprocessor-based system, including a control system 920 and a memory 970. The memory 970 may store parameters for various pacing, defibrillation, and sensing modes, along with other parameters. Further, the memory 970 may store data indicative of cardiac signals received by other components of the cardiac pacemaker/defibrillator 900. The memory 970 may be used, for example, for storing historical cardiac electrogram and therapy data. The historical data storage may include, for example, data obtained from long-term patient monitoring used for trending and/or other diagnostic purposes. Historical data, as well as other information, may be transmitted to an external programmer unit 990 as needed or desired.

The control system 920 and memory 970 may cooperate with other components of the cardiac pacemaker/defibrillator 900 to control the operations of the cardiac pacemaker/defibrillator 900. The control system 920 depicted in FIG. 9 incorporates activation sequence interval timing circuitry 926 configured to provide cardiac pacing response determination as described herein.

The control system 920 further includes a cardiac response classification processor 925 that works in conjunction with the pacing interval timing circuitry 926. The cardiac response classification processor 925 performs the function of analyzing the cardiac signal following pacing to determine the pacing response. For example, the cardiac response classification process may determine location of cardiac signal features with respect to one or more detection windows to determine the cardiac response to pacing.

The control system 920 may include additional functional components including a pacemaker control circuit 922, an arrhythmia detector 921, along with other components for controlling the operations of the cardiac pacemaker/defibrillator 900.

Telemetry circuitry 960 may be implemented to provide communications between the cardiac pacemaker/defibrillator 900 and an external programmer unit 990. In one embodiment, the telemetry circuitry 960 and the programmer unit 990 communicate using a wire loop antenna and a radio frequency telemetric link, as is known in the art, to receive and transmit signals and data between the programmer unit 990 and the telemetry circuitry 960. In this manner, programming commands and other information may be transferred to the control system 920 of the cardiac pacemaker/defibrillator 900 from the programmer unit 990 during and after implant. In addition, stored cardiac data pertaining to capture threshold, capture detection and/or cardiac response classification, for example, along with other data, may be transferred to the programmer unit 990 from the cardiac pacemaker/defibrillator 900.

The telemetry circuitry 960 may provide for communication between the cardiac pacemaker/defibrillator 900 and an advanced patient management (APM) system. The advanced patient management system allows physicians or other personnel to remotely and automatically monitor cardiac and/or other patient conditions. In one example, a cardiac pacemaker/defibrillator, or other device, may be equipped with various telecommunications and information technologies that enable real-time data collection, diagnosis, and treatment of the patient. Various embodiments described herein may be used in connection with advanced patient management.

Methods, structures, and/or techniques described herein, which may be adapted to provide for remote patient device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

In the embodiment of the cardiac pacemaker/defibrillator 900 illustrated in FIG. 9, electrodes RA-tip 856, RA-ring 854, RV-tip 812, RV-ring 811, RV-coil 814, SVC-coil 816, LV distal electrode 813, LV proximal electrode 817, LA distal electrode 818, LA proximal electrode 815, indifferent electrode 908, and can electrode 909 are coupled through a switch matrix 910 to sensing circuits 931-937.

A right atrial sensing circuit 931 serves to detect and amplify electrical signals from the right atrium of the heart. Bipolar sensing in the right atrium may be implemented, for example, by sensing voltages developed between the RA-tip 856 and the RA-ring 854. Unipolar sensing may be implemented, for example, by sensing voltages developed between the RA-tip 856 and the can electrode 909. Outputs from the right atrial sensing circuit are coupled to the control system 920.

A right ventricular sensing circuit 932 serves to detect and amplify electrical signals from the right ventricle of the heart. The right ventricular sensing circuit 932 may include, for example, a right ventricular rate channel 933 and a right ventricular shock channel 934. Right ventricular cardiac signals sensed through use of the RV-tip 812 electrode are right ventricular near-field signals and are denoted RV rate channel signals. A bipolar RV rate channel signal may be sensed as a voltage developed between the RV-tip 812 and the RV-ring 811. Alternatively, bipolar sensing in the right ventricle may be implemented using the RV-tip electrode 812 and the RV-coil 814. Unipolar rate channel sensing in the right ventricle may be implemented, for example, by sensing voltages developed between the RV-tip 812 and the can electrode 909.

Right ventricular cardiac signals sensed through use of the defibrillation electrodes are far-field signals, also referred to as RV morphology or RV shock channel signals. More particularly, a right ventricular shock channel signal may be detected as a voltage developed between the RV-coil 814 and the SVC-coil 816. A right ventricular shock channel signal may also be detected as a voltage developed between the RV-coil 814 and the can electrode 909. In another configuration the can electrode 909 and the SVC-coil electrode 816 may be electrically shorted and a RV shock channel signal may be detected as the voltage developed between the RV-coil 814 and the can electrode 909/SVC-coil 816 combination.

Left atrial cardiac signals may be sensed through the use of one or more left atrial electrodes 815, 818, which may be configured as epicardial electrodes. A left atrial sensing circuit 935 serves to detect and amplify electrical signals from the left atrium of the heart. Bipolar sensing and/or pacing in the left atrium may be implemented, for example, using the LA distal electrode 818 and the LA proximal electrode 815. Unipolar sensing and/or pacing of the left atrium may be accomplished, for example, using the LA distal electrode 818 to can vector 909 or the LA proximal electrode 815 to can vector 909.

A left ventricular sensing circuit 936 serves to detect and amplify electrical signals from the left ventricle of the heart. Bipolar sensing in the left ventricle may be implemented, for example, by sensing voltages developed between the LV distal electrode 813 and the LV proximal electrode 817. Unipolar sensing may be implemented, for example, by sensing voltages developed between the LV distal electrode 813 or the LV proximal electrode 817 and the can electrode 909.

Optionally, an LV coil electrode (not shown) may be inserted into the patient's cardiac vasculature, e.g., the coronary sinus, adjacent the left heart. Signals detected using combinations of the LV electrodes, 813, 817, LV coil electrode (not shown), and/or can electrodes 909 may be sensed and amplified by the left ventricular sensing circuitry 936. The output of the left ventricular sensing circuit 936 is coupled to the control system 920.

The outputs of the switching matrix 910 may be operated to couple selected combinations of electrodes 811, 812, 813, 814, 815, 816, 817, 818, 856, 854 to an evoked response sensing circuit 937. The evoked response sensing circuit 937 serves to sense and amplify signals developed using various combinations of electrodes for discrimination of various cardiac responses to pacing in accordance with embodiments of the invention. The cardiac response classification processor 925 analyzes the output of the evoked response sensing circuit 937 for implementation of cardiac pacing response classification.

Various combinations of pacing and sensing electrodes may be utilized in connection with pacing and sensing the cardiac signal following the pace pulses to determine the cardiac response to the pacing pulse. The pacemaker control circuit 922, in combination with pacing circuitry for the left atrium, right atrium, left ventricle, and right ventricle 941, 942, 943, 944, may be implemented to selectively generate and deliver pacing pulses to the heart using various electrode combinations. The pacing electrode combinations may be used to implement bipolar or unipolar pacing pulses to a heart chamber using one of the pacing vectors as described above.

In some implementations, the cardiac pacemaker/defibrillator 900 may include a sensor 961 that is used to sense the patient's hemodynamic need. In one implementation, the sensor may comprise, for example, an accelerometer configured to sense patient activity. In another implementation, the sensor may comprise an impedance sensor configured to sense patient respiration. The pacing output of the cardiac pacemaker/defibrillator may be adjusted based on the sensor output.

The electrical signal following the delivery of the pacing pulses may be sensed through various sensing vectors coupled through the switch matrix 910 to the evoked response sensing circuit 937 and/or other sensing circuits and used to classify the cardiac response to pacing. The cardiac response may be classified as one of left chamber capture only, right chamber capture only, multi-chamber capture, fusion and non-capture, for example.

The embodiments of the present invention described herein enhance the ability of a CRM device to perform automated threshold testing in the ambulatory patient. The described approaches can be used to provide automated threshold testing in a BiV configuration without interrupting the delivery of cardiac resynchronization therapy (CRT). Pacing in a BiV configuration during the threshold test provides automatic backup pacing in the event of loss of capture of one ventricle.

Additionally, automated threshold testing that changes the activation sequence by altering the pacing from BiV to single ventricular pacing may be proarrhythmic. The approaches described herein maintain BiV pacing and avoid the need to alter pacing to single chamber pacing to perform capture threshold testing.

Although the exemplary embodiments provided herein primarily relate to cardiac response determination for BiV pacing, the pacing interval adjustment to achieve a waveform that enhances cardiac response determination may be applied to any paces delivered to other heart chambers or to multiple sites within one heart chamber.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of determining a cardiac pacing response, comprising:
adjusting one or more pacing intervals to achieve at least one cardiac pacing response waveform morphology that enhances determination of the cardiac pacing response;
pacing a heart using the one or more adjusted pacing intervals; and
determining the cardiac response to the pacing.

2. The method of claim 1, wherein adjusting the one or more pacing intervals comprises adjusting an atrioventricular delay.

3. The method of claim 1, wherein adjusting the one or more pacing intervals comprises adjusting an interatrial delay.

4. The method of claim 1, wherein adjusting the one or more pacing intervals comprises adjusting an interventricular delay.

5. The method of claim 1, wherein adjusting the one or more pacing intervals comprises adjusting a delay between a first pace delivered to a first cardiac site of a heart chamber and a second pace delivered to a second cardiac site of the heart chamber.

6. The method of claim 1, wherein adjusting the one or more pacing intervals to achieve the at least one cardiac response waveform morphology that enhances determination of the cardiac pacing response comprises adjusting the one or more pacing intervals to enhance a difference between a first waveform morphology associated with multi-chamber capture and a second waveform morphology associated with single chamber capture.

7. The method of claim 1, wherein adjusting the one or more pacing intervals to achieve the at least one cardiac response waveform morphology that enhances determination of the cardiac pacing response comprises adjusting the one or more pacing intervals to enhance a difference between a first waveform morphology associated with capture of a heart chamber and a second waveform morphology associated with intrinsic depolarization of the heart chamber.

8. The method of claim 1, wherein pacing the heart using the adjusted pacing interval comprises pacing the heart using the adjusted pacing interval during a capture threshold test.

9. The method of claim 8, wherein adjusting the pacing interval comprises performing an initialization process prior to the capture threshold test to determine a value for the adjusted pacing interval that enhances the cardiac pacing response waveform morphology.

10. The method of claim 1, wherein:
pacing the heart comprises delivering bi-ventricular pacing; and
adjusting the one or more pacing intervals comprises adjusting one or both an atrioventricular delay and an interventricular delay to increase a morphological difference between a first waveform morphology indicative of single chamber ventricular capture and a second waveform morphology indicative of bi-ventricular capture.

11. The method of claim 1, wherein:
pacing the heart comprises delivering bi-ventricular pacing; and
adjusting the one or more pacing intervals comprises adjusting one or both an atrioventricular delay and an interventricular delay to increase a morphological difference between a first waveform morphology indicative of right ventricular capture only and a second waveform morphology indicative of bi-ventricular capture.

12. The method of claim 1, wherein:
pacing the heart comprises delivering multi-site pacing; and
adjusting the one or more intervals comprises adjusting one or more inter-site pacing delays to increase a morphological difference between a first waveform morphology indicative of single site capture and a second waveform morphology indicative of multi-site capture.

13. The method of claim 1, wherein adjusting the one more pacing intervals to achieve the at least one cardiac pacing response waveform morphology comprises adjusting the one or more pacing intervals to adapt for temporal drift of the at least one cardiac pacing response waveform morphology.

14. The method of claim 1, wherein adjusting the one more pacing intervals to achieve the at least one cardiac pacing response waveform morphology comprises adjusting the one or more pacing intervals to achieve the at least one cardiac pacing response waveform morphology that enhances cardiac pacing response determination in the presence of fusion or noise.

15. A cardiac rhythm management device, comprising:
pacing interval circuitry configured to time one or more pacing intervals and to adjust the one or more pacing intervals to obtain at least one cardiac response waveform that enhances cardiac pacing response determination;
a pulse generator coupled to the pacing interval circuitry and configured for pacing the heart using the one or more adjusted pacing intervals;
sensing circuitry configured to sense a cardiac signal; and
a processor coupled to the sensing circuitry and configured to determine the cardiac response to the pacing based on the sensed cardiac signal.

16. The device of claim 15, wherein:
the pacing interval circuitry is configured to adjust an atrioventricular delay; and
the pulse generator is configured to pace the heart using the adjusted atrioventricular delay.

17. The device of claim 15, wherein:
the pacing interval circuitry is configured to adjust an interventricular delay; and
the pulse generator is configured to pace the heart using the adjusted interventricular delay.

18. The device of claim 15, wherein:
the pacing interval circuitry is configured to adjust an intersite pacing interval between a first cardiac pacing site and a second cardiac pacing site; and
the pulse generator is configured to pace the heart using the adjusted intersite pacing interval.

19. The device of claim 15, wherein the pacing interval circuitry is configured to adjust the one or more pacing intervals to enhance a difference in a first waveform morphology associated with a first cardiac pacing response and a second waveform morphology associated with a second cardiac pacing response.

20. The device of claim 19, wherein:
the one or more pacing intervals comprises one or both an atrioventricular delay and an interventricular delay;
the first cardiac pacing response comprises biventricular capture; and
the second cardiac pacing response comprises right ventricular capture with loss of left ventricular capture.

21. The device of claim 15, wherein:
the pulse generator is configured to deliver multi-chamber pacing;
the sensing circuitry comprises at least one electrode disposed within a heart chamber, the sensing circuitry is configured to sense the cardiac signal using the at least one electrode; and
the processor is configured to discriminate between a multi-chamber cardiac pacing response and a single chamber cardiac pacing response based on the sensed cardiac signal.

22. The device of claim 21, wherein:
the at least one electrode comprises a right ventricular coil electrode;
the sensing circuitry is configured to sense the cardiac signal developed between the right ventricular electrode and a can electrode; and
the processor is configured to discriminate between biventricular capture and right ventricular capture with loss of left ventricular capture.

23. The device of claim 15, wherein:
the pulse generator is configured to deliver multi-site pacing within a heart chamber;
the sensing circuitry comprises at least one electrode disposed within the heart chamber, the sensing circuitry is configured to sense the cardiac signal using the at least one electrode; and
the processor is configured to discriminate between a multi-site cardiac pacing response and a single site cardiac pacing response based on the sensed cardiac signal.

24. The device of claim 15, further comprising control circuitry configured to perform a capture threshold test using the one or more adjusted pacing intervals.

25. The device of claim 15, further comprising control circuitry configured to perform beat to beat capture verification using the one or more adjusted pacing intervals.

26. The device of claim 15, wherein the processor is configured to provide one or more detection windows and to compare the sensed cardiac signal to the one or more capture detection windows to determine the cardiac pacing response.

27. A cardiac rhythm management device, comprising:
means for adjusting one or more pacing intervals to achieve at least one cardiac pacing response waveform morphology that enhances determination of the cardiac pacing response;
means for pacing a heart using the one or more adjusted pacing interval; and
means for determining the cardiac response to the pacing.

28. The device of claim 27, further comprising means for performing a capture threshold test using the one or more adjusted pacing intervals.

* * * * *